(12) United States Patent
Glombik et al.

(10) Patent No.: US 7,576,200 B2
(45) Date of Patent: Aug. 18, 2009

(54) DIPHENYLAZETIDINONES, PROCESS FOR THEIR PREPARATION, MEDICAMENTS COMPRISING THESE COMPOUNDS AND THEIR USE

(75) Inventors: Heiner Glombik, Hofheim (DE); Werner Kramer, Mainz-Laubenheim (DE); Stefanie Flohr, Eppstein (DE); Wendelin Frick, Hünstetten-Beuerbach (DE); Hubert Heuer, Schwabenheim (DE); Gerhard Jaehne, Frankfurt (DE); Andreas Lindenschmidt, Bad Soden (DE); Hans-Ludwig Schäfer, Hochheim (DE)

(73) Assignee: Sanofi-Aventis Deutschland GmbH, Frankfurt Am Main (DE)

( * ) Notice: Subject to any disclaimer, the term of this patent is extended or adjusted under 35 U.S.C. 154(b) by 0 days.

(21) Appl. No.: 12/219,196

(22) Filed: Jul. 17, 2008

(65) Prior Publication Data

US 2008/0281092 A1    Nov. 13, 2008

Related U.S. Application Data

(60) Continuation of application No. 11/797,720, filed on May 7, 2007, now Pat. No. 7,488,829, which is a division of application No. 11/155,109, filed on Jun. 17, 2005, which is a division of application No. 10/021,502, filed on Dec. 19, 2001, now Pat. No. 6,992,067.

(30) Foreign Application Priority Data

Dec. 21, 2000  (DE)  ................................. 100 64 398
Oct. 26, 2001  (DE)  ................................. 101 52 981

(51) Int. Cl.
*C07D 205/08*  (2006.01)
*C07D 263/20*  (2006.01)
*A61K 31/397*  (2006.01)
*A61K 31/70*  (2006.01)
*C07H 17/02*  (2006.01)

(52) U.S. Cl. ..................................................... 540/200
(58) Field of Classification Search .................. 540/200
See application file for complete search history.

(56) References Cited

U.S. PATENT DOCUMENTS

| 5,846,966 | A * | 12/1998 | Rosenblum et al. | 514/210.02 |
|---|---|---|---|---|
| 6,498,156 | B2 * | 12/2002 | Glombik et al. | 514/210.02 |
| 7,205,290 | B2 * | 4/2007 | Jaehne et al. | 514/210.02 |
| 7,388,004 | B2 * | 6/2008 | Jaehne et al. | 514/210.02 |
| 7,390,790 | B2 * | 6/2008 | Jaehne et al. | 514/23 |
| 7,407,938 | B2 * | 8/2008 | Jaehne et al. | 514/15 |
| 2004/0077623 | A1 * | 4/2004 | Jaehne et al. | 514/210.02 |
| 2007/0149501 | A1 * | 6/2007 | Jendralla et al. | 514/210.02 |
| 2008/0274947 | A1 * | 11/2008 | Jaehne et al. | 514/4 |

* cited by examiner

*Primary Examiner*—Mark L Berch
(74) *Attorney, Agent, or Firm*—Finnegan, Henderson, Farabow, Garrett & Dunner LLP

(57) ABSTRACT

Compounds of the formula I,

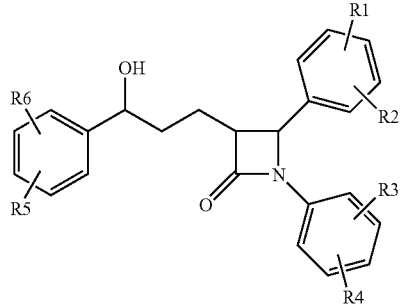

in which R1, R2, R3, R4, R5, and R6 have the meanings given in the description, and their physiologically acceptable salts. The compounds are suitable for use, for example, as hypolipidemics.

1 Claim, No Drawings

DIPHENYLAZETIDINONES, PROCESS FOR THEIR PREPARATION, MEDICAMENTS COMPRISING THESE COMPOUNDS AND THEIR USE

This is a continuation of application Ser. No. 11/797,720, filed May 7, 2007, now U.S. Pat. No. 7,488,829 which is a division of application Ser. No. 11/155,109, filed Jun. 17, 2005, which is a division of application Ser. No. 10/021,502, filed Dec. 19, 2001, issued as U.S. Pat. No. 6,992,067 on Jan. 31, 2006, and claims the benefit of priority of Federal Republic of Germany Application No. 10152981.3, filed Oct. 26, 2001, and Federal Republic of Germany Application No. 10064398.1, filed Dec. 21, 2000, all of which are incorporated herein by reference.

This application claims the benefit of priority under 35 U.S.C. § 119(a) to German patent application no. 10064398.1, filed on Dec. 21, 2000, and German patent application no. 10152981.3, filed on Oct. 26, 2001. The contents of both priority documents are incorporated by reference herein.

The invention relates to substituted diphenylazetidinones, to their physiologically acceptable salts and to derivatives having physiological function.

Diphenylazetidinones (such as, for example, ezetimibe) and their use for treating hyperlipidemia and arteriosclerosis and hypercholesterolemia have already been described [cf. Drugs of the Future 2000, 25(7):679-685 and U.S. Pat. No. 5,756,470].

It was an object of the invention to provide further compounds having a therapeutically utilizable hypolipidemic action. In particular it was an object to find novel compounds which, compared to the compounds described in the prior art, are absorbed to a very low extent. Very low absorption is to be understood as meaning an intestinal absorption of less than 10%, preferably less than or equal to 5%. In particular, absorption of the novel compounds should be less than that of ezetimibe. Pharmaceutically active compounds which are absorbed to a very low extent generally have considerably fewer side-effects.

Accordingly, an embodiment of the invention relates to compounds of the formula I,

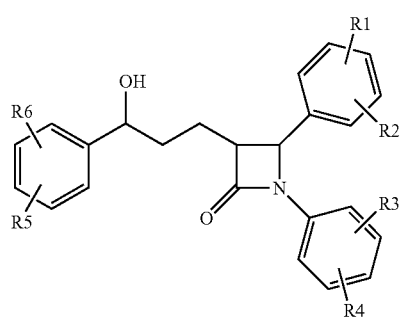

I in which

R1, R2, R3, R4, R5, R6 independently of one another are
 ($C_0$-$C_{30}$)-alkylene-(LAG), where one or more carbon atoms of the alkylene radical may be replaced by —O—, —(C=O)—, —CH=CH—, —C≡C—, —N(($C_1$-$C_1$-$C_6$)-alkyl), —N(($C_1$-$C_6$)-alkylpenyl) or —NH—; or
 H, F, Cl, Br, I, $CF_3$, $NO_2$, CN, COOH, COO($C_1$-$C_6$) alkyl, $CONH_2$, CONH($C_1$-$C_6$)-alkyl, CON[($C_1$-$C_6$)-alkyl]$_2$, ($C_1$-$C_6$)-alkyl, ($C_2$-$C_6$)-alkenyl, ($C_2$-$C_6$)-alkynyl or O—($C_1$-$C_6$)-alkyl, where one, more or all hydrogens in the alkyl radicals may be replaced by fluorine; or
$SO_2$—$NH_2$, $SO_2$NH($C_1$-$C_6$)-alkyl, $SO_2$N[($C_1$-$C_6$)-alkyl]$_2$, S—($C_1$-$C_6$)-alkyl, S—($CH_2$)$_n$-phenyl, SO—($C_1$-$C_6$)-alkyl, SO—($CH_2$)$_n$-phenyl, $SO_2$—($C_1$-$C_6$)-alkyl or $SO_2$—($CH_2$)$_n$-phenyl, where n=0–6 and the phenyl radical may be substituted up to two times by F, Cl, Br, OH, $CF_3$, $NO_2$, CN, $OCF_3$, O—($C_1$-$C_6$)-alkyl, ($C_1$-$C_6$)-alkyl or $NH_2$; or
$NH_2$, NH—($C_1$-$C_6$)-alkyl, N(($C_1$-$C_6$)-alkyl)$_2$, NH($C_1$-$C_7$-acyl, phenyl or O—($CH_2$)$_n$-phenyl, where n=0-6, where the phenyl ring may be mono- to trisubstituted by F, Cl, Br, I, OH, $CF_3$, $NO_2$, CN, $OCF_3$, O—($C_1$-$C_6$)-alkyl, ($C_1$-$C_6$)-alkyl, $NH_2$, NH($C_1$-$C_6$)-alkyl, N(($C_1$-$C_6$)-alkyl)$_2$, $SO_2$—$CH_3$, COOH, COO—($C_1$-$C_6$>alkyl or $CONH_2$;

(LAG) is a sugar residue, disugar residue, trisugar residue, tetrasugar residue;
 a sugar acid, an amino sugar;
 an amino acid residue, an oligopeptide residue comprising 2 to 9 amino acids; or
 a trialkylammoniumalkyl radical; or —O—($SO_2$)OH;

wherein at least one of the radicals R1 or R6 has the meaning ($C_0$-$C_{30}$)-alkylene-(LAG), where one or more carbon atoms of the alkylene radical may be replaced by —O—, —(C=O), —CH=CH—, —C≡C—, —N(($C_1$-$C_6$)-alkyl), —N(($C_1$-$C_6$)-alkylpenyl) or —NH—, and where the radicals R1 and R2 may not have the meaning —O-sugar residue or —O-sugar acid, and its pharmaceutically acceptable salts.

Another embodiment of the invention relates to compounds of the formula I, in which at least one of the radicals R1 to R6 has the meaning ($C_0$-$C_{30}$) alkylene-(LAG), where one or more carbon atoms of the alkylene radical may be replaced by —O—, —(C=O), —N(($C_1$-$C_6$)-alkyl), or —NH—.

Another embodiment of the invention relates to compounds of the formula I, in which one of the radicals R1 or R3 has the meaning ($C_0$-$C_{30}$)-alkylene-(LAG), where one or more carbon atoms of the alkylene radicals may be replaced by 4, —(C=O), —N($CH_3$), or —NH—.

Another embodiment of the invention relates to compounds of the formula I, in which one of the radicals R1 or R3 has the meaning —($CH_2$)$_{0-1}$—NH—(C=O)$_{0-1}$—($C_0$-$C_{25}$)-alkylene-(C=O)$_{0-1}$—N(R7)$_{0-1}$-(LAG); where one or more carbon atoms of the alkylene radical may be replaced by oxygen atoms and where R7 is H or $CH_3$.

Another embodiment of the invention relates to compounds of the formula I in which the group LAG is a mono-sugar residue.

A trialkylammonium alkyl radical is to be understood as meaning the following group

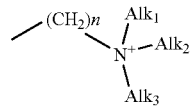

in which n=0 to 10 and $Alk_1$, $Alk_2$, $Alk_3$ independently of one another each denote a straight-chain or branched alkyl radical having 1 to 20 carbon atoms.

Owing to their increased solubility in water, compared to the parent compounds, pharmaceutically acceptable salts are particularly suitable for medical applications. These salts should have a pharmaceutically acceptable anion or cation. Suitable pharmaceutically acceptable acid addition salts of the compounds according to the invention are salts of inorganic acids, such as hydrochloric acid, hydrobromic acid, phosphoric acid, metaphosphoric acid, nitric acid, sulfonic acid and sulfuric acid, and of organic acids, such as acetic acid, benzenesulfonic acid, benzoic acid, citric acid, ethanesulfonic acid, fumaric acid, gluconic acid, glycolic acid, isothionic acid, lactic acid, lactobionic acid, maleic acid, malic acid, methanesulfonic acid, succinic acid, p-toluenesulfonic acid, tartaric acid and trifluoroacetic acid, for example. For medical purposes, very particular preference is given to using the chloride-salt. Suitable pharmaceutically acceptable basic salts are ammonium salts, alkali metal salts (such as sodium and potassium salts) and alkaline earth metal salts (such as magnesium and calcium salts).

The scope of the invention also includes salts having a pharmaceutically unacceptable anion, which salts may be useful intermediates for preparing or purifying pharmaceutically acceptable salts and/or for use in nontherapeutic, for example in vitro, applications.

Here, the term "derivative having physiological function" refers to any physiologically acceptable derivative of a compound according to the invention, for example an ester, capable of forming, upon administration to a mammal, for example man, to form such a compound or an active metabolite (directly or indirectly).

A further aspect of this invention are prodrugs of the compounds according to the invention. Such prodrugs can be metabolized in vivo to give a compound according to the invention. These prodrugs may or may not be active in their own right.

The compounds according to the invention can also be present in various polymorphous forms, for example as amorphous and crystalline polymorphous forms. The scope of the invention includes all polymorphous forms of the compounds according to the invention, which form a further aspect of the invention.

The compounds of the invention may also exist in the form of solvates. The compounds of the formula I and their pharmaceutically acceptable salts, esters and prodrugs and derivatives having physiological function are ideal medicaments for treating an impaired lipid metabolism, in particular hyperlipidemia. The compounds of the formula I are also suitable for modulating the serum cholesterol concentration and for treating arteriosclerotic manifestations. The compounds of the invention are also suitable for the treatment of insulin resistance.

As used here, "treatment" or "therapy" of a condition and "treating" a condition can mean successfully eliminating the condition, reducing the effects associated with it, and/or reducing its severity. It also includes administering the relevant compounds to a patient to avoid recurrence of a condition. It also includes avoiding the onset of a condition by administering the relevant compounds to patients falling into a risk group or category for developing the particular condition. Those skilled in the art can routinely identify patients likely to present with a given condition; thereby qualifying as candidates for treatment.

The compound(s) of the formula (I) can also be administered in combination with other active compounds.

The amount of a compound of the formula (I) required to achieve the desired biological effect depends on a number of factors, for example on the specific compound chosen, on the intended use, on the mode of administration and on the clinical condition of the patient. In general, the daily dose is in the range from 0.1 mg to 100 mg (typically from 0.1 mg to 50 mg) per day per kilogram of bodyweight, for example 0.1-10 mg/kg/day. Tablets or capsules may contain, for example, from 0.01 to 100 mg, typically from 0.02 to 50 mg. In the case of pharmaceutically acceptable salts, the abovementioned weight data relate to the weight of the diphenyl-azetidinone-ion derived from the salt. For the therapy of the above-mentioned conditions, the compounds of the formula (I) can be used themselves as the compound, but preferably they are present in the form of a pharmaceutical composition with an acceptable carrier. The carrier must of course be acceptable in the sense that it is compatible with the other constituents of the composition and is not harmful to the health of the patient. The carrier can be a solid or a liquid or both and is preferably formulated with the compound as an individual dose, for example as a tablet, which can contain from 0.05% to 95% by weight of the active compound. Further pharmaceutically active substances can also be present, including further compounds of the formula (I). The pharmaceutical compositions according to the invention can be prepared by one of the known pharmaceutical methods, which essentially consist in mixing the constituents with pharmacologically acceptable carriers and/or auxiliaries.

Pharmaceutical compositions according to the invention are those which are suitable for oral or peroral (e.g. sublingual) administration, although the most suitable manner of administration is dependent in each individual case on the nature and severity of the condition to be treated and on the type of the compound of the formula (I) used in each case. Coated formulations and coated delayed-release formulations are also included in the scope of the invention. Acid-resistant and enteric formulations are preferred. Suitable enteric coatings include cellulose acetate phthalate, polyvinyl acetate phthalate, hydroxypropylmethylcellulose phthalate and anionic polymers of methacrylic acid and methylmethacrylate.

Suitable pharmaceutical compounds for oral administration can be present in separate units, such as, for example, capsules, cachets, lozenges or tablets, which in each case contain a specific amount of the compound of the formula (I); as a powder or granules; as a solution or suspension in an aqueous or nonaqueous liquid; or as an oil-in-water or water-in-oil emulsion. As already mentioned, these compositions can be prepared according to any suitable pharmaceutical method which includes a step in which the active compound and the carrier (which can consist of one or more additional constituents) are brought into contact. In general, the compositions are prepared by uniform and homogeneous mixing of the active compound with a liquid and/or finely divided solid carrier, after which the product, if necessary, is shaped. For example, a tablet can thus be prepared by pressing or shaping a powder or granules of the compound, if appropriate with one or more additional constituents. Pressed tablets can be produced by tableting the compound in free-flowing form, such as, for example, a powder or granules, if appropriate mixed with a binder, lubricant, inert diluent and/or a (number of) surface-active/dispersing agent(s) in a suitable machine. Shaped tablets can be produced by shaping the pulverulent compound moistened with an inert liquid diluent in a suitable machine.

Pharmaceutical compositions which are suitable for per-oral (sublingual) administration include lozenges which contain a compound of the formula (I) with a flavoring, customarily sucrose and gum arabic or tragacanth, and pastiles which include the compound in an inert base such as gelatin and glycerol or sucrose and gum arabic.

Suitable other active compounds for the combination preparations include:

all antidiabetics, mentioned in Rote Liste 2001, Chapter 12, the disclosure of which is incorporated by reference herein. They can be combined with the compounds of the formula I according to the invention in particular to achieve a synergistically enhanced action. The active compound combination can be administered either by separate administration of the active compounds to the patient or in the form of combination preparations comprising a plurality of active compounds in a pharmaceutical preparation.

Antidiabetics include insulin and insulin derivatives, such as, for example, Lantus® or HMR 1964, GLP-1 derivatives, such as, for example, those disclosed by Novo Nordisk A/S in WO 98/08871, the disclosure of which is incorporated by reference herein, and oral hypoglycemic active compounds.

The oral hypoglycemic active compounds preferably include sulfonyl ureas, biguadines, meglitinides, oxadiazolidinediones, thiazolidinediones, glucosidase inhibitors, glucagon antagonists, GLP-1 agonists, potassium channel openers, such as, for example, those disclosed by Novo Nordisk A/S in WO 97/26265 and WO 99/03861, the disclosures of which are incorporated by reference herein, insulin sensitizers, inhibitors of liver enzymes involved in stimulating gluconeogenesis and/or glycogenolysis, modulators of glucose uptake, compounds which modulate lipid metabolism, such as antihyperlipidemic active compounds and antilipidemic active compounds, compounds which reduce food intake, PPAR and PXR agonists and active compounds which act on the ATP-dependent potassium channel of the beta cells.

In one embodiment of the invention, the compounds of the formula I are administered in combination with an HMGCoA reductase inhibitor such as simvastatin, fluvastatin, pravastatin, lovastatin, atorvastatin, cerivastatin, rosuvastatin.

In one embodiment of the invention, the compounds of the formula I are administered in combination with a cholesterol absorption inhibitor, such as, for example, ezetimibe, tiqueside, pamaqueside.

In one embodiment of the invention, the compounds of the formula I are administered in combination with a PPAR gamma agonist, such as, for example, rosiglitazone, pioglitazone, JTT-501, GI 262570.

In one embodiment of the invention, the compounds of the formula I are administered in combination with a PPAR alpha agonist, such as, for example, GW 9578, GW 7647.

In one embodiment of the invention, the compounds of the formula I are administered in combination with a mixed PPAR alpha/gamma agonist, such as, for example, GW 1536, AVE 8042, AVE 8134, AVE 0847.

In one embodiment of the invention, the compounds of the formula I are administered in combination with a fibrate, such as, for example, fenofibrate, clofibrate, bezafibrate.

In one embodiment of the invention, the compounds of the formula I are administered in combination with an MTP inhibitor, such as, for example, Bay 13-9952, BMS-201038, R-103757.

In one embodiment of the invention, the compounds of the formula I are administered in combination with a bile acid absorption inhibitor, such as, for example, HMR 1453.

In one embodiment of the invention, the compounds of the formula I are administered in combination with a CETP inhibitor, such as, for example, Bay 194789.

In one embodiment of the invention, the compounds of the formula I are administered in combination with a polymeric bile acid adsorber, such as, for example, cholestyramine, colesolvam.

In one embodiment of the invention, the compounds of the formula I are administered in combination with an LDL receptor inducer, such as, for example, HMR1171, HMR1586.

In one embodiment of the invention, the compounds of the formula I are administered in combination with an ACAT inhibitor, such as, for example, avasimibe.

In one embodiment of the invention, the compounds of the formula I are administered in combination with an antioxidant, such as, for example, OPC-14117.

In one embodiment of the invention, the compounds of the formula I are administered in combination with a lipoprotein lipase inhibitor, such as, for example, NO-1886.

In one embodiment of the invention, the compounds of the formula I are administered in combination with an ATP citrate lyase inhibitor, such as, for example, SB-204990.

In one embodiment of the invention, the compound the formula I are administered in combination with a squalene synthetase inhibitor, such as, for example, BMS-188494.

In one embodiment of the invention, the compounds of the formula I are administered in combination with a lipoprotein (a) antagonist, such as, for example, CI-1027 or nicotinic acid.

In one embodiment of the invention, the compounds of the formula I are administered in combination with a lipase inhibitor, such as, for example, Orlistat.

In one embodiment of the invention, the compounds of the formula I are administered in combination with insulin.

In one-embodiment, the compounds of the formula I are administered in combination with a sulfonyl urea, such as, for example, tolbutamide, glibenclamide, glipizide or gliclazide.

In one embodiment, the compounds of the formula I are administered in combination with a biguanide, such as, for example, metformin.

In another embodiment, the compounds of the formula I are administered in combination with a meglitinide, such as, for example, repaglinide.

In one embodiment, the compounds of the formula I are administered in combination with a thiazolidinedione, such as, for example, troglitazone, ciglitazone, pioglitazone, rosiglitazone, or the compounds disclosed by Dr. Reddy's Research Foundation in WO 97/41097, the disclosure of which is incorporated by reference herein, in particular 5-[[4-[(3,4-dihydro-3-methyl-4-oxo-2-quinazolinylmethoxy]phenyl]methyl]-2,4-thiazolidinedione.

In one embodiment, the compounds of the formula I are administered in combination with an α-glucosidase inhibitor, such as, for example, miglitol or acarbose.

In one embodiment, the compounds of the formula I are administered in combination with an active compound which acts on the ATP-dependent potassium channel of beta cells, such as, for example, tolbutamide, glibenclamide, glipizide, gliazide or repaglinide.

In one embodiment, the compounds of the formula I are administered in combination with more than one of the abovementioned compounds, for example in combination with a sulfonyl urea and metformin, a sulfonyl urea and acarbose, repaglinide and metformin, insulin and a sulfonyl urea, insulin and metformin, insulin and troglitazon, insulin and lovastatin, etc.

In a further embodiment, the compounds of the formula I are administered in combination with CART agonists, NPY agonists, MC4 agonists, orexin agonists, β3 agonists, TNF agonists, CRF agonists, CRF BP antagonists, urocortin agonists, β3-agonists, MSH (melanocyte-stimulating hormone) agonists, CCK agonists, serotonin reuptake inhibitors, mixed serotonin and noradrenergic compounds, 5HT agonists, bombesin agonists, galanin antagonists, growth hormone, growth hormone-releasing compounds, TRH agonists, decoupling protein 2- or 3 modulators, leptin agonists, DA agonists (bromocriptin, doprexin), lipase/amylase inhibitors, PPAR modulators, RXR modulators or TR-β agonists.

In one embodiment of the invention, the further active compound is leptin.

In one embodiment, the further active compound is dexamphetamine or amphetamine.

In one embodiment, the further active compound is fenfluramine or dexfenfluramine.

In another embodiment, the further active compound is sibutramine.

In one embodiment, the further active compound is Orlistat.

In one embodiment, the further active compound is mazindol or phentermine.

In one embodiment, the compounds of the formula I are administered in combination with fiber, preferably insoluble fiber, such as, for example, Caromax®. The combination with Caromax® can be given in one preparation or by separate administration of compounds of the formula I and Caromax®. Here, Caromax® can also be administered in the form of food, such as, for example, in bakery goods or muesli bars. Compared to the individual active compounds, the combination of compounds of the formula I with Caromax® is, in addition to an enhanced action, in particular with respect to the lowering of LDL cholesterol, also characterized by its improved tolerability.

It goes without saying that each suitable combination of the compounds according to the invention with one or more of the compounds mentioned above and optionally one or more further pharmacologically active substances is included in the scope of the present invention.

The invention furthermore provides both stereoisomer mixtures of the formula I and the pure stereoisomers of the formula I, and diastereomer mixtures of the formula I and the pure diastereomers. The mixtures are separated by chromatographic means.

Preference is given to both racemic and enantiomerically pure compounds of the formula I of the following structure:

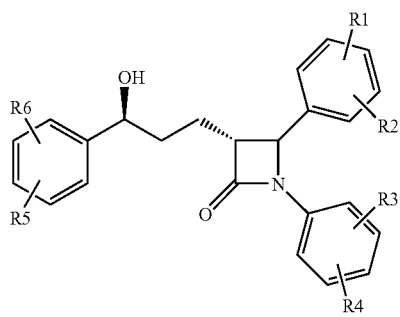

Sugar residues are to be understood as meaning compounds which are derived from aldoses and ketoses which have 3 to 7 carbon atoms and may belong to the D or the L series; also included are amino sugars, sugar alcohols or sugar acids. Glucose, mannose, fructose, galactose, ribose, erythrose, glyceroaldehyde, sedoheptulose, glucosamine, galactosamine, glucuronic acid, galacturonic acid, gluconic acid, galactonic acid, mannonic acid, glucamine, 3-amino-1,2-propanediol, glucaric acid and galactaric acid may be mentioned by way of example.

Disugars are saccharides composed of two sugar units. Di-, tri- or tetrasaccharides are formed by acetal-like binding of two or more sugars. Here, the bonds may be in the α- or β-form. Lactose, maltose and cellobiose may be mentioned by way of, example.

If the sugar is substituted, the substitution is preferably at the hydrogen atom of an OH group of the sugar.

Suitable protective groups for the hydroxyl groups of the sugars are substantially: benzyl, acetyl, benzoyl, pivaloyl, trityl, tert-butyldimethylsilyl, benzylidene, cyclohexylidene or isopropylidene protective groups.

The term "amino acids" or "amino acid residues" refers, for example, to the stereoisomeric forms, i.e. the D or L forms, of the following compounds:

| | | |
|---|---|---|
| alanine | glycine | proline |
| cysteine | histidine | glutamine |
| aspartic acid | isoleucine | arginine |
| glutamic acid | lysine | serine |
| phenylalanine | leucine | threonine |
| tryptophan | methionine | valine |
| tyrosine | asparagine | |
| 2-aminoadipic acid | | 2-aminoisobutyric acid |
| 3-aminoadipic acid | | 3-aminoisobutyric acid |
| beta-alanine | | 2-aminopimelic acid |
| 2-aminobutyric acid | | 2,4-diaminobutyric acid |
| 4-aminobutyric acid | | desmosine |
| piperidine carboxylic acid | | 2,2-diaminopimelic acid |
| 6-aminocaproic acid | | 2,3-diaminopropionic acid |
| 2-aminoheptanoic acid | | N-ethylglycine |
| 2-(2-thienyl)glycine | | 3-(2-thienyl)alanine |
| penicillamine | | sarcosine |
| N-ethylasparagine | | N-methylisoleucine |
| hydroxylysine | | 6-N-methyllysine |
| allo-hydroxylysine | | N-methylvaline |
| 3-hydroxyproline | | norvaline |
| 4-hydroxyproline | | norleucine |
| isodesmosine | | ornithine |
| allo-isoleucine | | |

N-methylglycine

For abbreviating the amino acids, the conventional notation was used (cf. Schröder, Lübke, The Peptides, Volume I, New York 1965, pages XXII-XXIII; Houben-Weyl, Methoden der Organischen Chemie [Methods of organic chemistry], Volume XV/1 and 2, Stuttgart 1974). The amino acid pGlu denotes pyroglutamyl, Nal denotes 3-(2-naphthyl)alanine, azagly-NH$_2$ denotes a compound of the formula NH$_2$NH—CONH$_2$ and D-Asp denotes the D form of aspartic acid. According to their chemical nature, peptides are acid amides, and on hydrolysis they decompose into amino acids.

An oligopeptide is to be understood as meaning a peptide constructed of 2 to 9 of the amino acids mentioned above.

Suitable protective groups (see, for example, T. W. Greene, "Protective Groups in Organic Synthesis") for amino acids are primarily:

Arg(Tos), Arg(Mts), Arg(Mtr), Arg(PMV), Asp(OBzl), Asp (OBut), Cys(4-MeBzl), Cys(Acm), Cys(SBut), Glu(Obzl), Glu(Obut), His(Tos), His(Fmoc), His(Dnp), His(Trt), Lys (Cl-Z), Lys(Boc), Met(O), Ser(Bzl), Ser(But), Thr(Bzl), Thr (But), Trp(Mts), Trp(CHO), Tyr(Br-Z), Tyr(Bzl) or Tyr(But).

Amino protective groups that are preferably used are the benzyloxycarbonyl (Z) radical, which can be removed by catalytic hydrogenation, the 2-(3,5-dimethyloxyphenyl)propyl(2)oxycarbonyl(Ddz) or trityl (Trt) radical, which can be removed by weak acids, and the 9-fluorenylmethyloxycarbonyl (Fmoc) radical, which can be removed using secondary amines.

The invention furthermore relates to a process for preparing diphenylazetidinone derivatives of formula I.

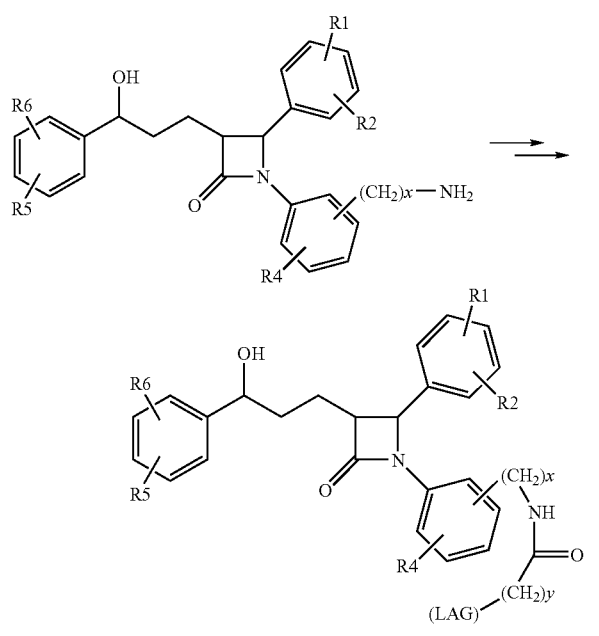

Independently of one another, x and y can be from 0 to 10. In compound II, —(CH$_2$)x-NH$_2$ may alternatively also be attached to one of the other two phenyl rings.

The process for preparing the compounds of the formula I comprises reacting an amine of the formula II with an alkylating or acylating agent which, preferably in the omega position, carries a further functionality—if appropriate in protected form. This functionality is (after deprotection) used for attaching (LAG), for example with the formation of ether, amine or amide bonds.

The examples below serve to illustrate the invention in more detail, without limiting the invention to the products and embodiments described in the examples.

EXAMPLE I

N-4-[3-(3-Hydroxy-3-phenylpropyl)-2-(4-methoxyphenyl-4-oxoazetidin-1-yl]-benzyl-5-(2,3,4,5,6-pentahydroxyhexylamino)pentanamide (3)

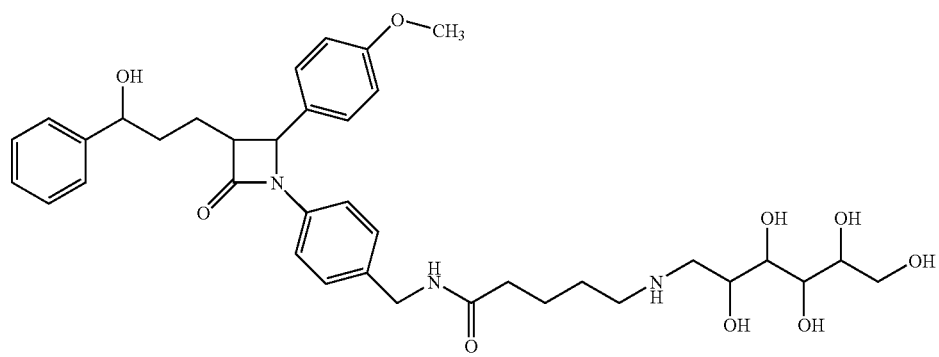

a) N-4-[3-(3-Hydroxy-3-phenylpropyl)-2-(4-methoxyphenyl)-4-oxoazetidin-1-yl]-benzyl-5-bromopentanamide (2)

416 mg of 1-(4-aminomethylphenyl)-3-(3-hydroxy-3-phenylpropyl)-4-(4-methoxy-phenyl)azetidin-2-one (1) are dissolved in 10 ml of dried dichloromethane, and 0.2 ml of triethylamine is added. With ice-cooling, 200 mg of 5-bromovaleryl chloride, dissolved in 2 ml of dichloromethane, are added, and the mixture, stirred at room temperature for 5 hours. 5 ml of water are added, the mixture is acidified using 0.5 N HCl (pH ~3), the phases are separated, the aqueous phase is washed with a little dichloromethane, the combined organic solutions are dried with sodium sulfate and the residue is, after removal of the solvent, purified by silica gel column filtration. This gives 2 as an oil of molecular weight 579.54 (C$_{31}$H$_{35}$BrN$_2$O$_4$) MS (FAB): 581/579 (M+H$^+$).

b) N-4-[3-(3-Hydroxy-3-phenylpropyl)-2-(4-methoxyphenyl-4-oxoazetidin-1-yl]benzyl-5-(2,3,4,5,6-pentahydroxyhexylamino)pentanamide (3)

300 mg of 2 are dissolved in 10 ml of dimethylformamide, and 191 mg of 6-aminohexane-1,2,3,4,5-pentaol are added. The mixture is stirred at 80° C. until the reaction (monitored by thin-layer chromatography) has substantially ended (after about 2 hours). The solvent is then removed under reduced pressure and the residue is chromatographed on silica gel (mobile phase: CH$_2$Cl$_2$/methanol/conc. ammonia=30:10:2). This gives 3 of molecular weight 679.82 (C$_{37}$H$_{49}$N$_3$O$_9$); MS (FAB): 680 (M+H$^+$).

EXAMPLE II

N-4-1-(4-Fluorophenyl)-3-[3-(4-fluorophenyl)-3-hydroxypropyl]-1-oxoazetidin-2-yl}benzyl-2,3,4,5,6-pentahydroxyhexanamide (4)

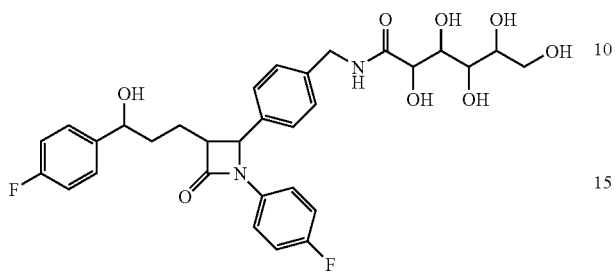

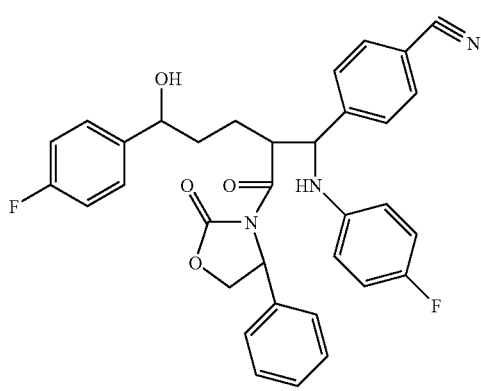

a) 4-[5-(4-Fluorophenylyl)-(4-fluorophenylamino)-5-hydroxy-2-(2-oxo-4-phenyl-oxazolidin-3-carbonyl)pentyl]benzonitrile (5)

Under argon, 2.5 g of 3-[5-(4-fluorophenyl)-5-hydroxy-pentanoyl]-4-phenyl-oxazolidin-2-one are dissolved in 30 ml of dichloromethane, 3.9 g of 4-[4-fluoro-phenylimino)methyl]benzonitrile are added and the mixture is cooled to −10° C. 6.4 ml of diisopropylethylamine are added to this mixture and then, over a period of 3 min. 4.05 ml of trimethylsilyl chloride such that the temperature does not exceed −5° C. At this temperature, the mixture is stirred for another hour, and it is then cooled to −25° C. 0.8 ml of titanium tetrachloride is then added slowly. The dark mixture is stirred at −25 to −30° C. overnight and then decomposed using 35 ml of 7% strength tartaric acid solution, and stirring is continued at room temperature for 1 hour. 15 ml of a 20% strength sodium bicarbonate solution are then added, and the mixture is stirred for another hour. Following phase separation, the org. phase is washed with 30 ml of water, dried over magnesium sulfate and concentrated to about 10 ml. After addition of 2 ml of bistrimethylsilylacetamide, the mixture is heated at reflux for 30 min and then concentrated under reduced pressure. The residue is crystallized with ethyl acetate/heptane. The product is filtered off with suction and dried under reduced pressure. This gives 5 of molecular weight 653.81 ($C_{37}H_{37}F_2N_3O_4Si$); MS (ESI+): 654.3 (M+H$^+$), 582.2 (M+H$^+$-Si(CH$_3$)$_3$).

b) {1-(4-Fluorophenyl)-3-[3-(4-fluorophenyl)-3-hydroxypropyl]-4-oxoazetidin-2-yl}benzonitrile (6)

2 g of 5 are dissolved in 20 ml of methyl tert-butyl ether and, with 100 mg of tetrabutylammonium fluoride trihydrate and 1.3 ml of bistrimethylsilylacetamide, heated at 40° C. for about 1 h. The reaction is monitored by thin-layer chromatography. After the reaction has ended, initially 0.2 ml of glacial acetic acid is added, and the mixture is stirred for 30 min and concentrated. The residue is treated with 20 ml of a mixture of isopropanol/2N sulfuric acid=10:1 and stirred for 1 hour. Following the addition of a spatula tip of solid sodium bicarbonate, the mixture is once more concentrated under reduced pressure, the residue is taken up in ethyl acetate, the org. phase is washed with water and dried and the residue is, after removal of the solvent, purified by column chromatography (SiO$_2$, CH$_2$Cl$_2$/methanol=100:1). This gives 6 of molecular weight 418.45 ($C_{25}H_{20}F_2N_2O_2$); MS (DCl+): 419 (M+H$^+$).

c) 4-(4-Aminomethylphenyl)-1-(4-fluorophenyl)-3-[3-(4-fluorophenyl)-3-hydroxypropyl]azetidin-2-one (7)

200 mg of 6 are dissolved in 20 ml of ethanol and, with 0.5 ml of conc. ammonia, hydrogenated over Raney nickel at a hydrogen pressure of 75 bar and at 25° C. for 30 hours. The catalyst is filtered off with suction, the filtrate is concentrated under reduced pressure and the residue is purified by column filtration (SiO$_2$, CH$_2$Cl$_2$/methanol/conc. NH$_3$=100:10:1). This gives 7 of molecular weight 422.5 ($C_{25}H_{22}F_2N_2O_2$); MS (DCl+): 423 (M+H$^+$), 405 (M+H$^+$-H$_2$O).

d) N-4-{1-(4-Fluorophenyl)-3-[3-(4-fluorophenyl)-3-hydroxypropyl]-4-oxoazetidin-2-yl}benzyl-2,3,4,5,6-pentahydroxyhexanamide (4)

50 mg of 7 and 25 mg of 3,4,5-trihydroxy-6-hydroxymethyltetrahydropyran-2-one are dissolved in 5 ml of methanol and, together with 10 mg of Na$_2$CO$_3$, stirred overnight. The mixture is filtered off with suction, the filtrate is concentrated under reduced pressure and the residue is purified by column filtration (SiO$_2$, CH$_2$Cl$_2$/methanol=10:1). This gives 4 having a melting point above 180° C. and the molecular weight 600.6 ($C_{31}H_{34}F_2N_2O_8$); MS (ESI+): 601 (M+H$^+$), 583 (M+H$^+$-H$_2$O).

EXAMPLE III

N-4-[3-[3-(4-Fluorophenyl)-3-hydroxypropyl]-2-(4-methoxyphenyl)-4-oxoazetidin-yl]benzyl-12-(2,3,4,5,6-pentahydroxyhexanoylamino)dodecanamide (8)

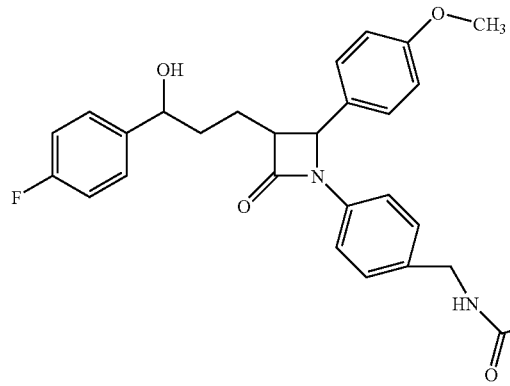

a)
12-(2,3,4,5,6-Pentahydroxyhexanoylamino)dodecanoic acid (9)

3.5 g of 12-aminododecanoic acid are dissolved in 500 ml of methanol and, with 2.7 g of finely powdered sodium carbonate and 4.8 g of 3,4,5-trihydroxy-6-hydroxymethyltetrahydropyran-2-one, stirred at room temperature for 30 hours. The mixture is filtered off, the filtrate is concentrated and the residue is dissolved in 70 ml of water. With ice-cooling, 1N hydrochloric acid is added gradually until the pH is 1-2 (about 50-55 ml). The free acid precipitates out and is filtered off with suction, washed with a little cold water, and dried under high vacuum at 35° C. This gives 9 of molecular weight 393.48 ($C_{18}H_{35}NO_8$); MS (ESI+): 394 (M+H$^+$); (ESI−):392 (M−H)$^−$.

b) N-4-[3-[3-(4-Fluorophenyl)-3-hydtoxypropyl]-2-(4-methoxyphenyl)-4-oxoazetidin-1-yl]benzyl-12-(2,3,4,5,6-pentahydroxyhexanoylamino)dodecanamide (8)

is prepared similarly to Example II, starting from 1-(4-aminomethylphenyl)-(3-hydroxy-3-phenylpropyl)-4-(4-methoxyphenyl)azetidin-2-one. This gives N-4-[3-[3 hydroxy-3-phenylpropyl)-2-(4-methoxyphenyl)-4-oxoazetidin-1-yl] benzyl-12-(2,3,4,5,6-pentahydroxyhexanoylamino) dodecanamide of melting point 100° C. and molecular weight 792 ($C_{44}H_{61}N_3O_{10}$); MS (ESI+): 792 (M+H$^+$).

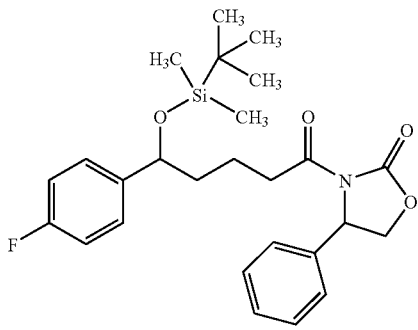

3-[5-(tert-Butyldimethylsilanyloxy)-5-(4-fluorophenyl)pentanoyl]-phenyloxazolidin-2-one (10)

30 g of 3-[5-(4-Fluorophenyl)-5-hydroxypentanoyl]-4-phenyloxazolidin-2-one are dissolved in 50 ml of DMF. 14.3 g of imidazole and 19 g of tert-butyldimethylsilyl chloride in 25 ml of DMF are added, and the mixture is then stirred at room temperature until the reaction has gone to completion (2-4 h). The reaction solution is concentrated, water is added and the mixture is extracted with ethyl acetate. The organic phase is dried over magnesium sulfate and concentrated, giving 10:
$C_{26}H_{34}FNO_4Si$ (471.65) MS (ESI) 494 (M+Na)

3-[(4-Fluorophenylimino)methyl]benzonitrile (11)

88 ml of para-fluoroaniline are added dropwise to 12 g of meta-cyanobenzaldehyde in 60 ml of isopropanol. After 1 h at 60° C., the product precipitates out. The mixture is allowed to warm to room temperature and filtered off, and the residue is washed with isopropanol. Drying gives 11 of m.p. 101° C.
$C_{14}H_9FN_2$ (224.24).

3-[5-(tert-Butyldimethylsilanyloxy)-5-(4-fluorophenyl)-1-(4-fluorophenylamino)-2-(2-oxo-4-phenyloxazolidine-3-carbonyl)pentyl]benzonitrile (12)

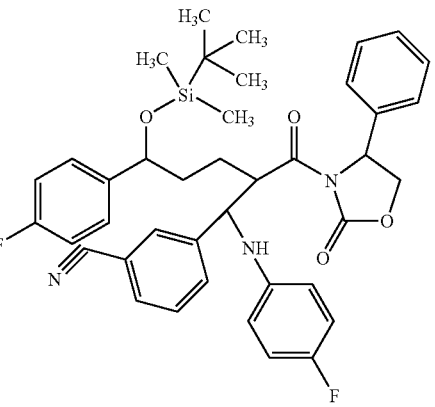

At 10° C., 24 ml of diisopropylethylamine are added to 14 g of 3-[5-(tert-butyldimethyl-silanyloxy)-5-(4-fluorophenyl)pentanoyl]-4-phenyloxazolidin-2-one (1 and 12.5 g of 3-[(4-fluorophenylimino)methyl]benzonitrile 11 in 200 ml of methylene chloride, and 7.1 ml of trimethylsilyl chloride are added dropwise. After 1 h, 3.4 ml of titanium tetrachloride are added dropwise at −10° C. The mixture is stirred at −10° C. for 3 h and then allowed to stand at −30° C. for another 12 h. 8 ml of acetic acid and 140 ml of a 7% strength aqueous tartaric acid solution are then added, and stirring is continued at room temperature for another 2 h. 50 ml of 20% strength aqueous sodium hydrogen sulfite solution are added, and the mixture is then stirred for another hour and extracted with methylene chloride. The organic phase is dried over magnesium sulfate, concentrated and purified by silica gel chromatography (ethyl acetate/heptane 1/3->1/1). This gives 12

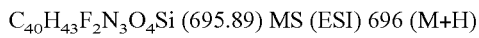

$C_{40}H_{43}F_2N_3O_4Si$ (695.89) MS (ESI) 696 (M+H)

3-[3-[3-(tert-Butyldimethylsilanyloxy)-3-(4-fluorophenyl)propyl]-1-(4-fluorophenyl)-4-oxoazetidin-2-yl]benzonitrile (13)

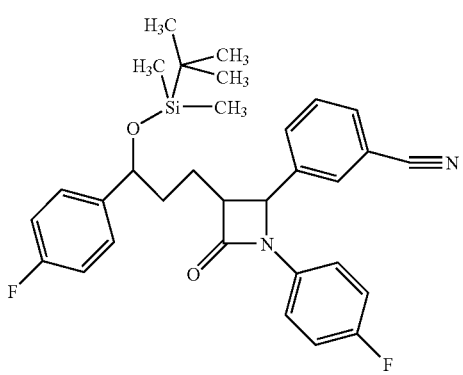

Under argon, a mixture of 13 g of 3-[5-(tert-butyldimethylsilanyloxy)-5-(4-fluorophenyl)-1-(4-fluorophenylamino)-2-(2-oxo-4-phenyloxazolidine-3-carbonyl)pentyl]benzonitrile 12, 50 ml of bistrimethylsilylacetamide, 0.5 g of tetrabutylammonium fluoride and 100 ml of tert-butyl methyl ether is stirred at room temperature for 10 h. After the reaction has ended, 5 ml of acetic add are added slowly with ice-cooling, and the mixture is concentrated. The residue is separated by silica gel chromatography (ethyl acetate/heptane=⅛). This gives 13:

$C_3H_{34}F_2N_2O_2Si$ (532.71) MS (ESI) 555 (M+Na)

3-{1-(4-Fluorophenyl)-3-[3-(4-fluorophenyl)-3-hydroxypropyl]-4-oxoazetidin-2-yl}-benzonitrile (14)

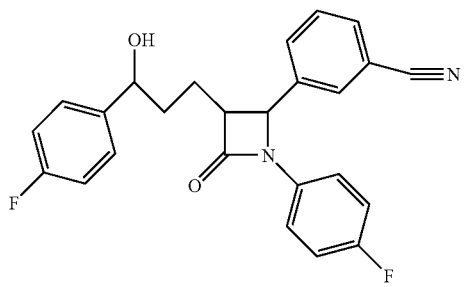

10 ml of 1N hydrochloric acid are added to 7.8 g of 3-[3-[3-(tert-butyldimethyl-silanyloxy)-3-(4-fluorophenyl)propyl]-1-(4-fluorophenyl)-4-oxoazetidin-2-yl]benzonitrile (13) in 200 ml of methanol, and the mixture is stirred for 12 h. Aqueous sodium bicarbonate solution is added to the reaction mixture, which is then extracted with methylene chloride. The organic phase is dried over magnesium sulfate, concentrated and purified by silica gel chromatography (ethyl acetate/heptane=1/3->1/1). This gives 14: $C_{25}H_{20}F_2N_2O_2$ (418.45) MS (ESI) 401 (M+H-H$_2$O)

EXAMPLE IV 4-(3-Aminomethylphenyl)-1-(4-fluorophenyl)-3-[3-(4-fluorophenyl)-3-hydroxypropyopyl]-azetidin-2-one (15)

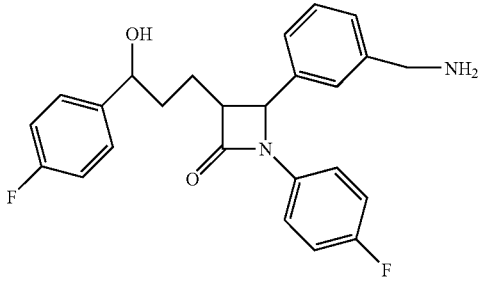

In an autoclave, at a hydrogen pressure of 75 bar, 2.5 g of 3-{1-(4-fluorophenyl)-3-[3-(4-fluorophenyl)-3-hydroxypropyl]-4-oxoazetidin-2-yl}benzonitrile 5 are reacted in 100 ml of ethanol and 15 ml of concentrated ammonia with 1.0 g of Raney-Nickel for 20 h. The reaction solution is filtered, concentrated and separated by silica gel chromatography (methylene chloride/methanol=10/1). This gives 15: $C_{25}H_{24}F_2N_2O_2$ (422.48) MS (ESI) 405 (M+H—H$_2$O)

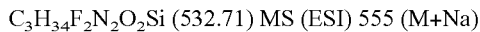

EXAMPLE V

N-3-{2-(4-Fluorophenyl)-4-[3-(4-fluorophenyl)-3-hydroxypropyl]-4-oxoazetidin-2-yl}-benzyl-2,3,4,5,6-pentahydroxyhexanamide (16)

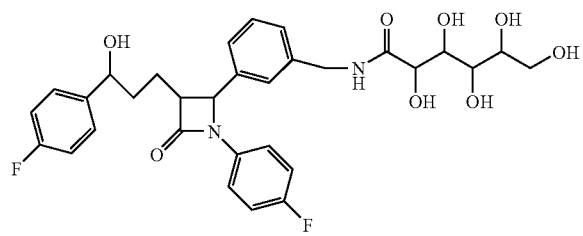

25 mg of sodium carbonate are added to a solution of 100 mg of 4-(3-aminomethyl-phenyl)-1-(4-fluorophenyl)-3-[3-(4-fluorophenyl)-3-hydroxypropyl]azetidin-2-one 6 and 46 mg of 3,4,5-trihydroxy-6-hydroxymethyltetrahydropyran-2-one in 5 ml of methanol, and the mixture is stirred at room temperature until the reaction has gone to completion. The reaction solution is filtered and concentrated. The residue is purified by HPLC (Knauer Eurospher-100-10-C18, water (0.1% trifluoroacetic acid)/acetonitrile (0.1% trifluoroacetic acid)=80/20->10/90). This gives 16:

$C_{31}H_{34}F_2N_2O_8$ (600.62) MS (ESI) 601 (M+H)

EXAMPLE VI

[3-(3-{2-(4-Fluorophenyl)-4-[3-(4-fluorophenyl)-3-hydroxypropyl]-4-oxoazetidin-2-yl}-benzylcarbamoyl)propyl]trimethylammonium 2,2,2-trifluoroacetate (17)

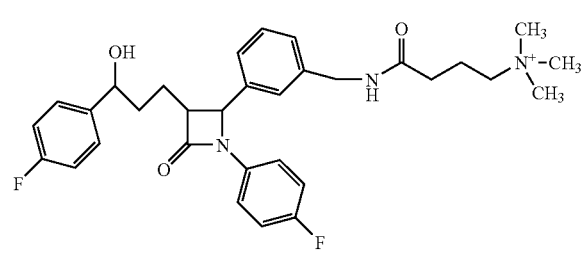

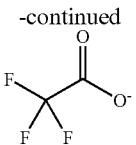

A solution of 100 mg of 4-(3-aminomethylphenyl)-1-(4-fluorophenyl)-3-[(4 fluorophenyl)-3-hydroxypropyl]azetidin-2-one (15), 64 mg of 3-carboxypropyl-trimethylammonium chloride, 93 µl of diisopropylcarbodiimide, 65 mg of hydroxybenzotriazole and 60 µl of diisopropylethylamine in 2 ml of methylene chloride is stirred at room temperature for 12 h. Water is added, and the mixture is extracted with methylene chloride. The organic phase is dried over magnesium sulfate, concentrated and separated by HPLC (Knauer Eurospher-100-10-C18, water (0.1% trifluoroacetic acid)/acetonitrile (0.1% trifluoroacetic acid)=80/20->10/90). This gives 17: $C_{32}H_{35}F_2N_3O_3$ (550.67) MS (ESI) 551: (M+H)

EXAMPLE VII

[3-(3-{2-(4-Fluorophenyl)-4-[3-(4-fluorophenyl)-3-hydroxypropyl]-4-oxoazetidin-2-yl}benzylcarbamoyl)-2-hydroxypropyl]trimethylammonium 2,2,2-trifluoroacetate (18)

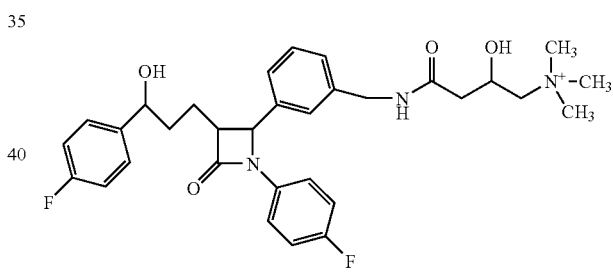

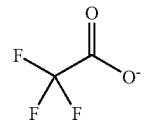

18 is prepared similarly to 17 starting from 100 mg of 4-(3-aminomethylphenyl)-1-(4-fluorophenyl)-3-[3-(4-fluorophenyl)-3-hydroxypropyl]azetidin-2-one 15, 64 mg of (3-carboxy-2-hydroxypropyl)trimethylammonium chloride, 93 µl diisopropylcarbodiimide, and 65 mg of hydroxybenzotriazole in 2 ml of methylene chloride. Without any extraction step, the reaction solution is concentrated and then purified by HPLC (Merck-Hibar-Lichrospher 100-RP-18, water (0.1% trifluoroacetic acid)/acetonitrile (0.1% trifluoroacetic acid)= 80/20->10/90). This gives 18:

$C_{32}H_{38}F_2N_3O_4$ (566.67) MS (ESI) 567 (M+H)

EXAMPLE VIII

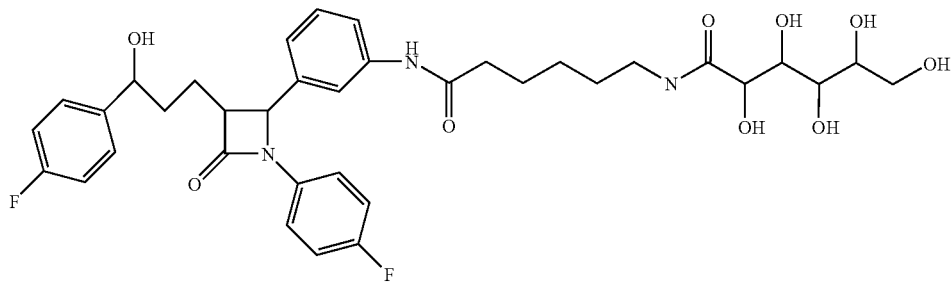

N-[5-(3-{1-(4-Fluorophenyl)-3-[3-(4-fluorophenyl)-3-hydroxypropyl]-4-oxoazetidin-2-yl}phenylcarbamoyl)pentyl]-2,3,4,5,6-pentahydroxyhexanamide (19)

19 is prepared similarly to 18 starting from 100 mg of 4-(3-aminomethylphenyl)-1-(4-fluorophenyl)-3-[3-(4-fluorophenyl)-3-hydroxypropyl]azetidin-2-one 15,108 mg of 6-(2,3,4,5,6-pentahydroxyhexanoylamino)hexanoic acid, 93 µl of diisopropylcarbodiimide and 65 mg of hydroxybenzotriazole in 2 ml of methylene chloride. This gives 10:

$C_{37}H_{45}F_2N_3O_9$ (713.78) MS (ESI) 714 (M+H)

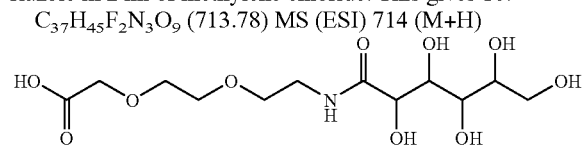

{2-[2-(2,3,4,5,6-Pentahydroxyhexanoylamino)ethoxy]ethoxy}acetic acid (20)

172 mg of sodium carbonate are added to a solution of 450 mg of [2-(2-aminoethoxy)ethoxy]acetic acid and 318 mg of 3,4,5-trihydroxy-hydroxymethyltetrahydropyran-2-one in 10 ml of methanol, and the mixture is stirred at room temperature until the reaction has gone to completion. The reaction solution is filtered and concentrated. The residue is taken up in water and acetonitrile (1/1), resulting in the formation of 2 phases. The aqueous phase is concentrated and contains 20:

$C_{12}H_{23}NO_{10}$ (341.32) MS (ESI) 342 (M+H)

EXAMPLE IX

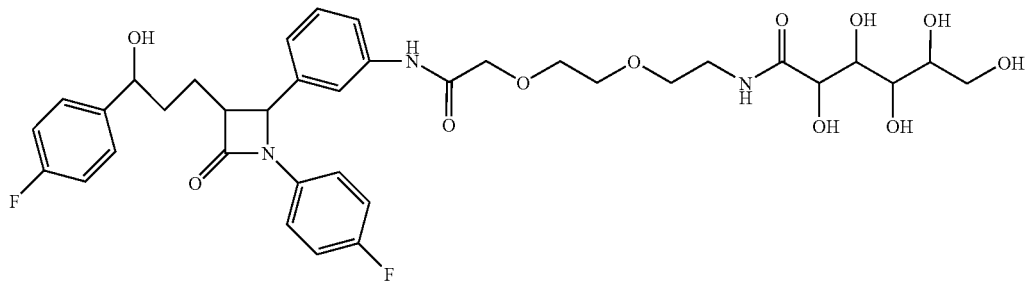

N-(2-{2-[(3-{1-(4-Fluorophenyl)-3-[3-(4-fluorophenyl)-3-hydroxypropyl]-4-oxoazetidin-2-yl}benzylcarbamoyl)methoxy]ethoxy}ethyl)-2,3,4,5,6-pentahydroxyhexanamide (21)

21 is prepared similarly to 18 starting from 100 mg of 4-(3-aminomethylphenyl)-1-(4-fluorophenyl)-3-[3-(4-fluorophenyl)-3-hydroxypropyl]azetidin-2-one (15), 122 mg of {2-[2-(2,3,4,5,6-pentahydroxyhexanoylamino)ethoxy]ethoxy}acetic acid (20), 93 µl of diisopropylcarbodiimide and 65 mg of hydroxybenzotriazole in 2 ml of dimethylformamide. This gives 21: $C_{37}H_{45}F_2N_3O_{11}$ (745.78) MS (ESI) 746 (M+H)

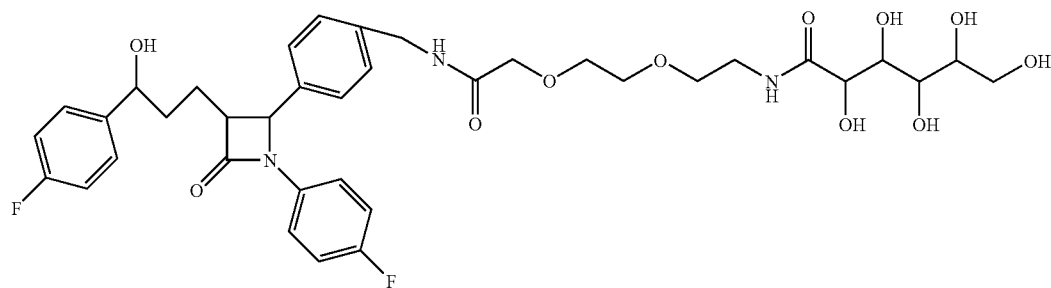

EXAMPLE X

N-(2-{2-[(4-{1-(4-Fluorophenyl)-3-[3-(4-fluorophenyl)-3-hydroxypropyl]-4-oxoazetidin-2-yl}benzylcarbamoyl)methoxy]ethoxy}ethyl)-2,3,4,5,6-pentahydroxyhexanamide (22)

22 is prepared similarly to 18 starting from 100 mg of 4-(4-aminomethylphenyl)-1-(4-fluorophenyl)-3-[3-(4-fluorophenyl)-3-hydroxypropyl]azetidin-2-one, 122 mg of {2-[2-(2,3,4,5,6-pentahydroxyhexanoylamino)ethoxy]ethoxy}acetic acid 20, 93 µl of diisopropylcarbodiimide and 65 mg of hydroxybenzotriazole in 2 ml of dimethylformamide and 1 ml of acetonitrile. This gives 22:

$C_{37}H_{45}F_2N_3O_{11}$ (745.78) MS (ESI) 746 (M+H)

2,3,4-Triacetoxy-1-{2-[2-(2-aminoethoxy)ethoxy]acetyl}-5-hydroxypentyl acetate (23)

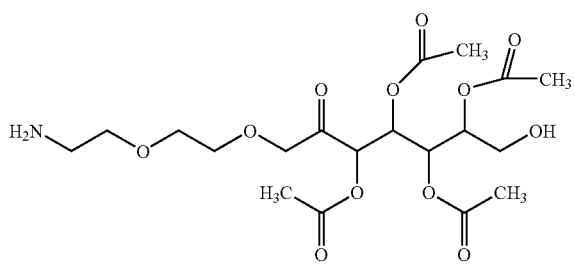

In a hydrogenation apparatus, a suspension of 1.12 g of 2,3,4-triacetoxy-1-{2-[2-(2-azido-ethoxy)ethoxy]acetyl}5-hydroxypentyl acetate and 1.0 g of Raney-Nickel in 100 ml of ethanol is shaken under an atmosphere of hydrogen for 4 h. The reaction solution is filtered and concentrated. The residue contains 23:

$C_{20}H_{33}NO_{12}$ (479.49) MS (ESI) 480 µM+H)

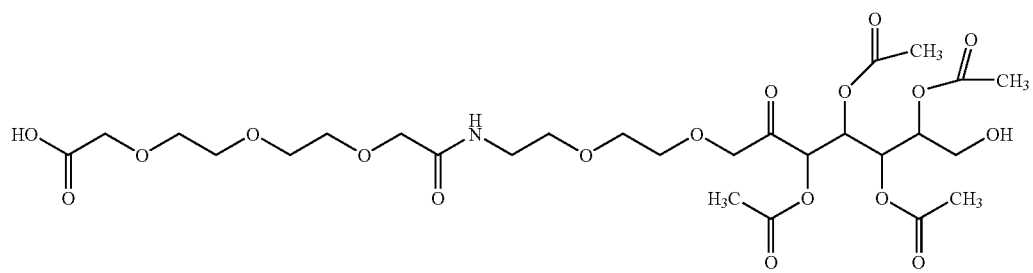

{2-[2-({2-[2-(3,4,5,6-Tetraacetoxy-7-hydroxy-2-oxoheptyloxy)ethoxy]ethylcarbamoyl}-methoxy)ethoxy]ethoxy}acetic acid (24)

A solution of 500 mg of 2,3,4-triacetoxy-1-{2-[2-(2-aminoethoxy)ethoxy]acetyl}5 hydroxypentyl acetate 23, 1.15 g of [2-(2-carboxymethoxyethoxy)ethoxy]acetic acid, 400 µl of diisopropylcarbodiimide and 288 mg of hydroxybenzotriazole in 20 ml of methylene chloride is stirred at room temperature for 12 h. The reaction solution is concentrated and separated by HPLC (Knauer Eurospher-100-10-C18, water (0.1% trifluoroacetic acid)/acetonitrile (0.1% trifluoroacetic acid)=80/20->10/90). This gives 24: $C_{28}H_{45}NO_{18}$ (683.67) MS (ESI) 684 (M+H)

[2-({2-[2-(3,4,5,6-Tetraacetoxy-7-hydroxy-2-oxoheptyloxy)ethoxy]ethylcarbamoyl}-methoxy)ethoxy]acetic acid (25)

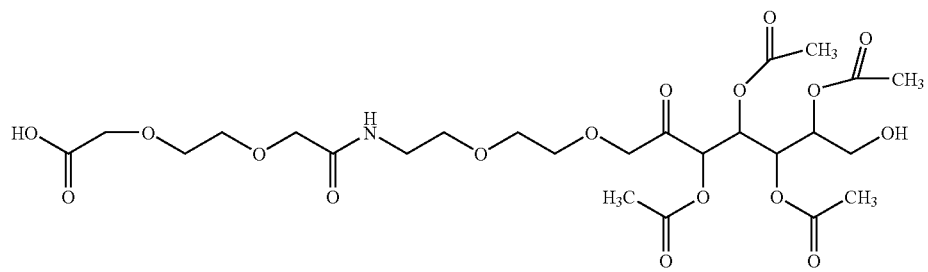

25 is prepared similarly to 24 starting from 500 mg of 2,3,4-triacetoxy-1-{2-[2-(2-aminoethoxy)ethoxy]acetyl}-5-hydroxypentyl acetate 23, 927 mg of (2-carboxymethoxyethoxy)acetic acid, 400 µl of diisopropylcarbodiimide and 288 mg of hydroxybenzotriazole in 20 ml of methylene chloride. This gives 25:

$C_{26}H_{41}NO_{17}$ (639.61) MS (ESI) 640 (M+H)

{2-[2-({2-[2-(3,4,5,6,7-Pentahydroxy-2-oxoheptyloxy)ethoxy]ethylcarbamoyl}-methoxy)ethoxy]ethoxy}acetic acid (26)

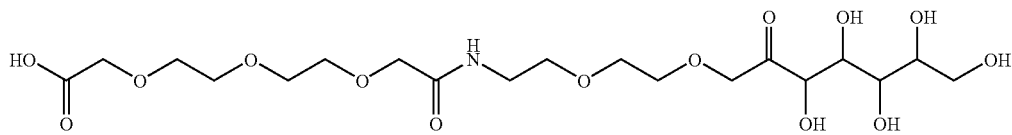

At room temperature, 100 µl of a 5.4 M sodium methoxide solution in methanol are added to a solution of 200 mg of {2-[2-({2-[2-(3,4,5,6-tetraacetoxy-7-hydroxy-2-oxo-heptyloxy)ethoxy]ethylcarbamoyl}methoxy)ethoxy]ethoxy}acetic acid (24) in 5 ml of methanol, and the mixture is stirred for 2 h. 1 g of Amberlite IR 120 is added to the reaction solution and the mixture is stirred for 10 min, filtered and concentrated, giving 26:

$C_{20}H_{37}NO_{14}$ (515.52) MS (ESI) 516 (M+H)

[2-({2-[2-(3,4,5,67-Pentahydroxy-2-oxoheptyloxy) ethoxy]ethylcarbamoyl}methoxy)-ethoxy]acetic acid (27)

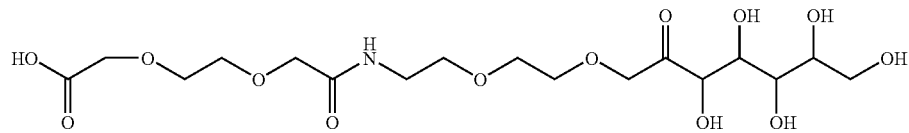

27 is prepared similarly to 26 starting from 200 mg of 25. This gives 27:
C$_{26}$H$_{41}$N$_{1}$O$_{17}$ (471.46) MS (ESI) 472 (M+H)

EXAMPLE XI

N-(4-{1-(4-Fluorophenyl)-3-[3-(4-fluorophenyl)-3-hydroxypropyl]-4-oxoazetidin-2-yl}-benzyl)-2-{2-[2-({2-[2-(3,4,5,6,7-pentahydroxy-2-oxoheptyloxy) ethoxy]ethyl-carbamoyl}methoxy)ethoxy] ethoxy}acetamide (28)

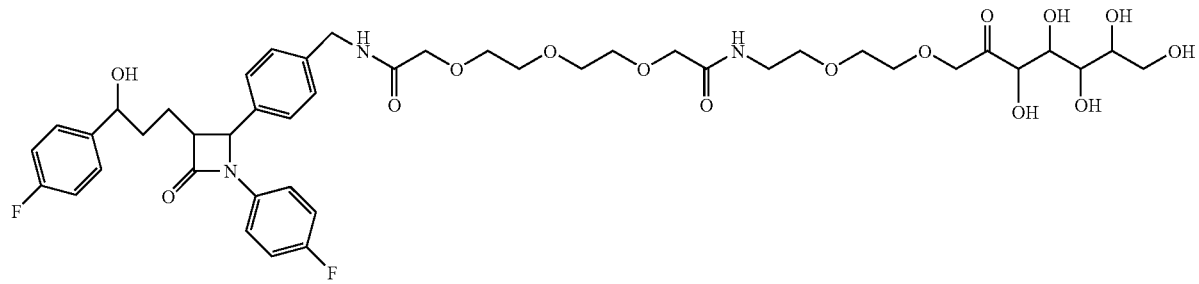

28 is prepared similarly to 18 starting from 62 mg of 4-(4-aminomethylphenyl)-1-(4-fluorophenyl)-3-[3-(4-fluorophenyl)-3-hydroxypropyl]azetidin-2-one, 76 mg of {2-[2-({2-[2-(3,4,5,6,7-pentahydroxy-2-oxoheptyloxy)ethoxy] ethylcarbamoyl}methoxy)ethoxy]ethoxy}acetic acid 17, 57 µl of diisopropylcarbodiimide and 40 mg of hydroxybenzotriazole in 2 ml of dimethylformamide. This gives 19:
C$_{45}$H$_{59}$F$_{2}$N$_{3}$O$_{14}$ (919.98) MS (ESI) 920 (M+H)

EXAMPLE XI

N-(3-{1-(4-Fluorophenyl)-3-[3-(4-fluorophenyl)-3-hydroxypropyl]-4-oxoazetidin-2-yl}-benzyl)-2-{2-[2-({2-[2-(3,4,5,6,7-pentahydroxy-2-oxo-heptyloxy) ethoxy]ethyl carbamoyl}methoxy)ethoxy] ethoxy}acetamide (29)

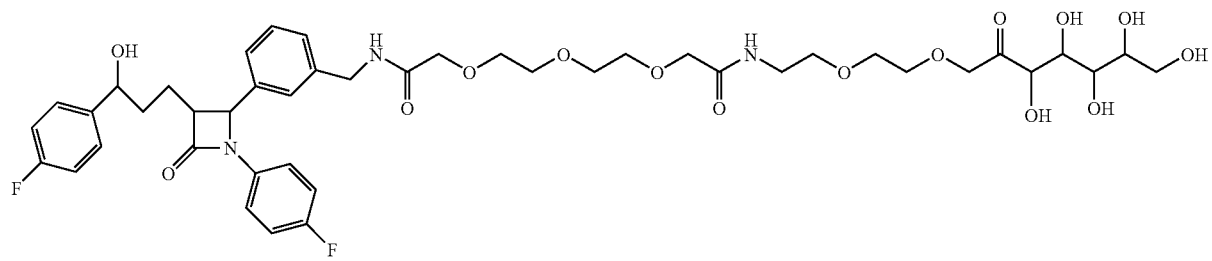

29 is prepared similarly to 18 starting from 62 mg of 4-(3-aminomethylphenyl)-1-(4-fluorophenyl)-3-[3-(4-fluorophenyl)-hydroxypropyl]azetidin-2-one 15, 76 mg of {2-[2-({2-[2-(3,4,5,6,7-pentahydroxy-2-oxoheptyloxy)ethoxy] ethylcarbamoyl}methoxy)ethoxy]ethoxy}acetic acid 26, 57 µl of diisopropylcarbodiimide and 40 mg of hydroxybenzotriazole in 2 ml of dimethylformamide. This gives 19: $C_{45}H_{59}F_2N_3O_{14}$ (919.98) MS (ESI) 920 (M+H)

EXAMPLE XIII

N-(4-{1-(4-Fluorophenyl)-3-[3-(4-fluorophenyl)-3-hydroxypropyl]-4-oxoazetidin-2-yl}-benzyl)-2-[2-({2-[2-(3,4,5,6,7-pentahydroxy-2-oxoheptyloxy) ethoxy]-ethylcarbamoyl}-methoxy)ethoxy] acetamide (30)

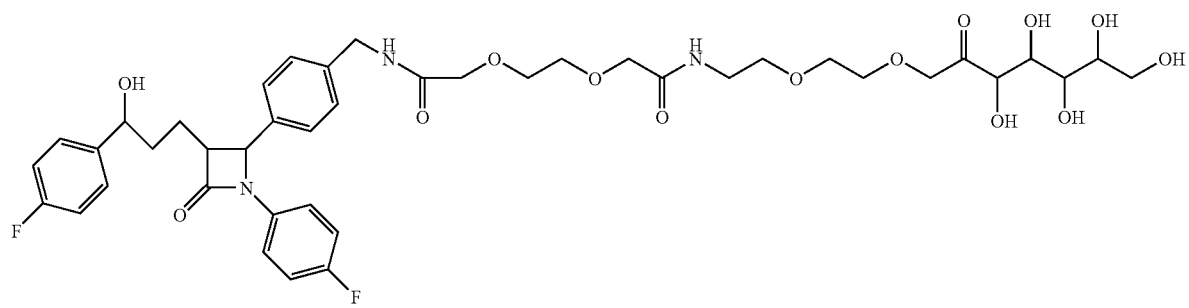

30 is prepared similarly to 18 starting from 68 mg of 4-(4-aminomethylphenyl)-1-(4-fluorophenyl)-3-[3-(4-fluorophenyl)-3-hydroxypropyl]azetidin-2-one 76 mg of [2-({2-[2-(3,4,5,6,7-pentahydroxy-2-oxoheptyloxy)ethoxy] ethylcarbamoyl}methoxy)ethoxy]acetic acid (27, 62 µl of diisopropylcarbodiimide and 44 mg of hydroxybenzotriazole in 2 ml of dimethylformamide. This gives 30: $C_{43}H_{55}F_2N_3O_{14}$ (875.93) MS (ESI) 876 (M+H)

EXAMPLE XIV

N-(3-{1-(4-Fluorophenyl)-3-[3-(4-fluorophenyl)-3-hydroxypropyl]-4-oxoazetidin-2-yl}-benzyl)-2-[2-({2-[2-(3,4,5,6,7-pentahydroxy-2-oxoheptyloxy) ethoxy]ethylcarbamoyl}-methoxy)ethoxy]acetamide (31)

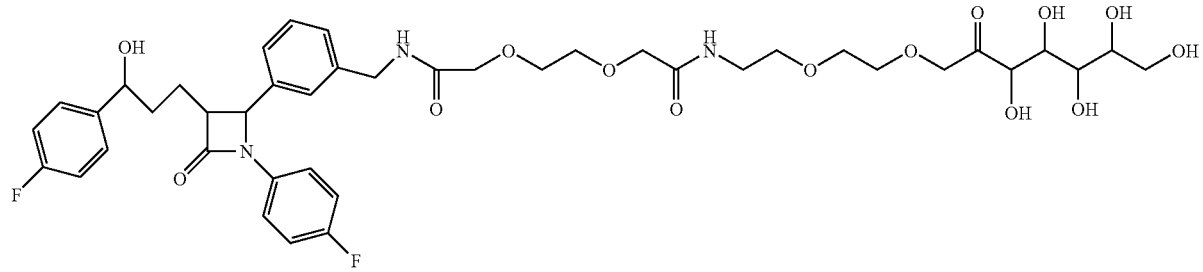

31 is prepared similarly to 18 starting from 68 mg of 4-(3-aminomethylphenyl)-1-(4-fluorophenyl)-3-[3-(4-fluorophenyl)-3-hydroxypropyl]azetidin-2-one (15), 76 mg of [2-({2-[2-(3,4,5,6,7-pentahydroxy-2-oxoheptyloxy)ethoxy] ethylcarbamoyl}methoxy)-ethoxy]acetic acid (27), 62 µl of diisopropylcarbodiimide and 44 mg of hydroxybenzotriazole in 2 ml of dimethylformamide. This gives 31: $C_{43}H_{55}F_2N_3O_{14}$ (875.93) MS (ESI) 876 (M+H)

EXAMPLE XV

[3-(4-{1-(4-Fluorophenyl)-3-[3-(4-fluorophenyl)-3-hydroxypropyl]-4-oxoazetidin-2-yl}benzylcarbamoyl)propyl]trimethylammonium trifluoroacetate (32)

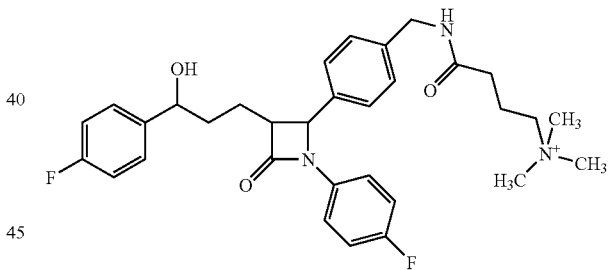

-continued

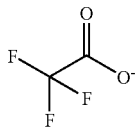

91 mg of (3-carboxypropyl)trimethylammonium chloride are dissolved in 5 ml of dimethylformamide, and the solution is cooled to 0° C. 0.055 ml of N-methylmorpholine, 210 mg of 4-(4-aminomethylphenyl)-1-(4-fluorophenyl)-3-[3-(4-fluorophenyl)-3-hydroxypropyl]azetidin-2-one, 77 mg of N-hydroxybenzotriazole and 96 mg of 1-ethyl-3-(3-dimethylaminopropyl)carbodiimide hydrochloride are added successively, and the reaction solution is warmed to room temperature and stirred for 12 h. The reaction mixture is concentrated under reduced pressure and the residue is taken up in sat. sodium bicarbonate solution, stirred and concentrated under reduced pressure. Repeatedly, this residue is stirred in acetone and the suspension is filtered. The combined filtrates are concentrated and purified chromatographically (RP18; acetonitrile/water ½, with 0.1% trifluoroacetic acid). This gives [3-(4-{1-(4-fluorophenyl)-3-[3-(4-fluorophenyl)-3-hydroxypropyl]-4-oxoazetidin-2-yl}benzylcarbamoyl)propyl]trimethylammonium; trifluoroacetate of molecular weight 550.67 ($C_{32}H_{38}F_2N_3O_3$; cation); MS (ESI): 551.24 (M+H$^+$).

EXAMPLE XVI

Dodecyl-[3-(4-{1-(4-fluorophenyl)-3-[3-(4-fluorophenyl)-3-hydroxypropyl]-4-oxoazetidin-2-yl}benzylcarbamoyl)propyl]dimethylammonium trifluoroacetate (33)

The compound of Example XVI is obtained like that of Example XV, with the difference that, instead of (3-carboxypropyl)trimethylammonium chloride, (3-carboxypropyl)dodecyldimethylammonium chloride is used. This gives dodecyl-[3-(4-{1-(4-fluorophenyl)-3-[3-(4-fluorophenyl)-3-hydroxypropyl]-4-oxoazetidin-2-yl}benzylcarbamoyl)propyl]dimethylammonium trifluoroacetate of molecular weight 703.96 ($C_{43}H_{69}F_2N_3O_3$; cation); MS (ESI): 704.70 (M+H$^+$).

EXAMPLE XVII

Dodecyl-[10-(4-{1-(4-fluorophenyl)-3-[3-(4-fluorophenyl)-3-hydroxypropyl]-4-oxoazetidin-2-yl}benzylcarbamoyl)decyl]dimethylammonium trifluoroacetate (34)

The compound of Example XVII is obtained like that of Example XV, with the difference that, instead of (3-carboxypropyl)trimethylammonium chloride, (10-carboxydecyl)dodecyldimethylammonium chloride is used. This gives dodecyl-[10-(4-{1-(4-fluorophenyl)-3-[3-(4-fluorophenyl)-3-hydroxypropyl]-4-oxoazetidin-2-yl}benzylcarbamoyl)de-

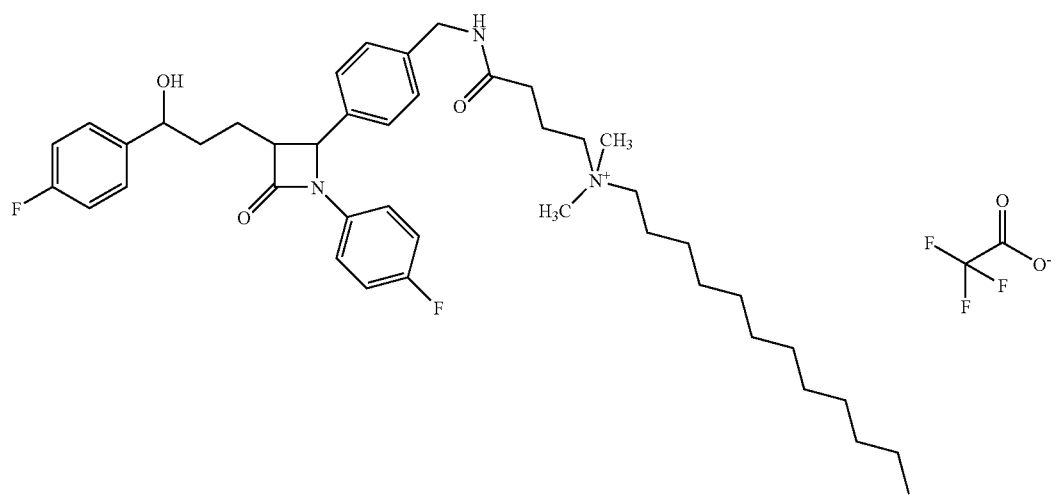

cyl]dimethylammonium trifluoroacetate of molecular weight 803.16 ($C_{50}H_{74}F_2N_3O_3$; cation); MS (ESI): 803.77 ($M^+$).

EXAMPLE XVIII

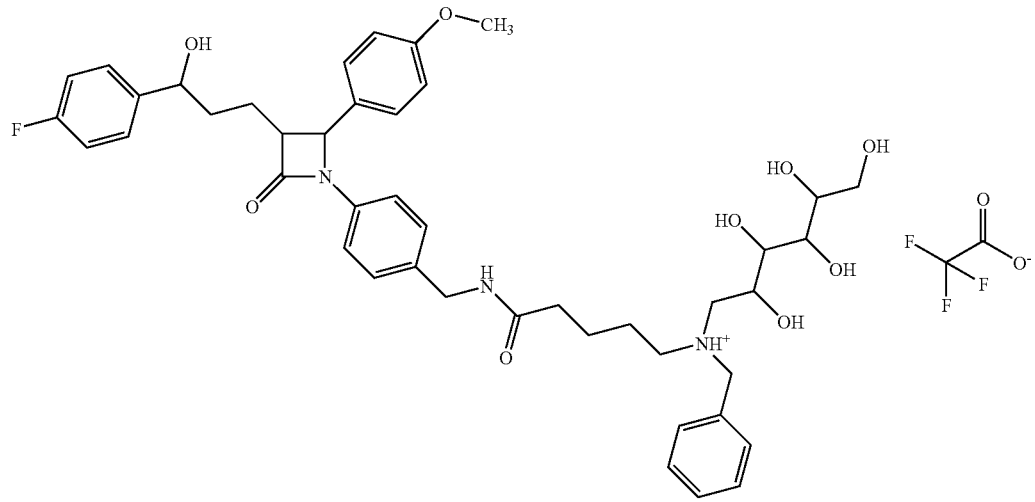

Benzyl-(4-{4-[3-[3-(4-fluorophenyl)-3-hydroxypropyl]-2-(4-methoxyphenyl)-4-oxoazetidin-1-yl] benzylcarbamoyl}butyl)-(2,3,4,5,6-pentahydroxyhexyl)ammonium trifluoroacetate (35)

a) Methyl 5-[benzyl-(2,3,4,5,6-pentahydroxyhexyl) amino]pentanoate (36)

At room temperature, 1.37 g of 6-benzylaminohexane-1, 2,3,4,5-pentanol are suspended in 30 ml of dry dimethylformamide, 1.45 g of potassium carbonate, 0.83 g of potassium iodide and 0.86 ml of methyl 5-bromovalerate are added and the mixture is stirred at room temperature overnight. The next day, the reaction mixture is filtered and the filtrate is concentrated under reduced pressure and, for purification, subjected to chromatography (silica gel; ethyl acetate/methanol/water 5/1/0.1). This gives methyl 5-[benzyl-(2,3,4,5,6-pentahydroxyhexyl)amino]-pentanoate of molecular weight 385.46 ($C_{19}H_{31}NO_7$); MS (ESI): 386.33 ($M+H^+$).

b) 5-[Benzyl-(2,3,4,5,6-pentahydroxyhexyl)amino] pentanoic acid (37)

At room temperature, 0.46 g of methyl 5-[benzyl(2,3,4,5, 6-pentahydroxyhexyl)-amino]pentanoate is dissolved in a mixture of 5 ml of ethanol and 5 ml of water, 0.4 g of potassium hydroxide is added and the mixture is stirred at 80° C. for 2 h. The cooled reaction mixture is then concentrated under reduced pressure and the residue is taken up in water, neutralized with hydrochloric acid and again concentrated. The crude product is suspended in ethanol, the suspension is filtered and the filtrate is concentrated under reduced pressure. This gives 5-[benzyl-(2,3,4,5,6-pentahydroxyhexyl) amino]pentanoic acid of molecular weight 371.43 ($C_{18}H_{29}NO_7$); MS (ESI): 372.2 ($M+H^+$).

c) 3-[5-(tert-Butyldimethylsilanyloxy)-5-(4-fluorophenyl)pentanoyl]-4-phenyloxazolidin-2-one (38)

27 g of 3-[(4-fluorophenyl)-5-hydroxypentanoyl]-4-phenyloxazolidin-2-one, 13.6 g of tert-butyldimethylsilyl chloride and 10.2 g of imidazole are dissolved in 36 ml of dimethylformamide, and the mixture is stirred at 60° C. for 90 min. After the reaction has ended, the mixture is dissolved in ethyl acetate and extracted twice with water. The organic phase is dried over magnesium sulfate, filtered and concentrated under reduced pressure. This gives 3-[5-(tert-butyldimethylsilanyloxy)-5-(4-fluorophenyl)-pentanoyl]-4-phenyloxazolidin-2-one of molecular weight 471.65 ($C_{26}H_{34}FNO_4Si$); MS (ESI): 340.28 ($MH^+$-$HOSi(CH_3)_2C(CH_3)_3$).

d) 4-[5-(tert-Butyldimethylsilanyloxy)-5-(4-fluorophenyl)-1-(4-methoxyphenyl)-2-(2 oxo-4-phenyloxazolidine-3-carbonyl)pentylamino]benzonitrile (39)

16.2 g of 3-[5-(tert-butyldimethylsilanyloxy)-5-(4-fluorophenyl)pentanoyl]-4-phenyl-oxazolidin-2-one are dissolved in 350 ml of dichloromethane. 19.8 ml of Hünig base and 10.14 g of 4-[(4-methoxyphenylamino)methyl]benzonitrile are added, and the solution is cooled to −10° C. 85.2 ml of trimethylsilyl triflate are added to the cooled solution, which is stirred at −10° C. for 30 min. The solution is then cooled to −30° C., and 44 ml of titanium tetrachloride solution are added. The reaction mixture is stirred at from −30 to 40° C. for 2 h. The reaction solution is then allowed to warm to room temperature and washed successively with 200 ml of 2N sulfuric-acid, 300 ml of 20% strength sodium hydrogensulfite solution and sat. sodium chloride solution. The organic phase is dried over magnesium sulfate and concentrated under reduced pressure, and the residue is purified on silica gel using n-heptane/ethyl acetate 3/1. This gives 4-[5-(tert-butyldimethylsilanyloxy)-5-(4-fluorophenyl)-1-(4-methoxyphenyl)-2-(2-oxo-4-phenyloxazolidine-3-carbonyl)pentylamino]benzonitrile of molecular weight 707.93 ($C_{41}H_{46}FN_3O_5Si$); MS (ESI): 590.51 ($MH^+$-$C_7H_5N_2$);

e) 4-[3-[3-(tert-Butyldimethylsilanyloxy)-3-(4-fluorophenyl)propyl]-2-(4-methoxyphenyl)-4-oxo-azetidin-1-yl]benzonitrile (40)

13.2 g. of 4-[5-(tert-butyldimethylsilanyloxy)-5-(4-fluorophenyl)-1-(4-methoxyphenyl)-2-(2-oxo-4-phenyloxazolidine-3-carbonyl)pentylamino]benzonitrile are dissolved in 380 ml of methyl tert-butyl ether, 18.6 ml of N,O-bis(trimethylsilyl)acetamide and 1.86 ml of a 1 M solution of tetrabutylammonium fluoride in tetrahydrofuran are added and the mixture is stirred at room temperature for 2 h. After the reaction has ended, 10 ml of acetic acid are added, the reaction mixture is concentrated under reduced pressure and the residue is purified on silica gel using toluene/ethyl acetate 50/1. This gives 4-[3-[3-(tert-butyldimethylsilanyloxy)-3-(4-fluorophenyl)propyl]-2-(4-methoxyphenyl)-4-oxoazetidin-1-yl]benzonitrile of molecular weight 544.75 ($C_{32}H_{37}FN_2O_3Si$); MS (ESI): 545.56 (M+H$^+$).

f) 4-[3-[3-(4-Fluorophenyl)-3-hydroxypropyl]-2-(4-methoxyphenyl)-4-oxoazetidin-1-yl]benzonitrile (41)

3.5 g of 4-[3-[3-(tert-butyldimethylsilanyloxy)-3-(4-fluorophenyl)propyl]-2-(4-methoxyphenyl)-4-oxoazetidin-1-yl]benzonitrile are dissolved in 65 ml of tetrahydrofuran, 0.74 ml of acetic acid and 8.03 ml of a 1 M solution of tetrabutylammonium fluoride in tetrahydrofuran are added, and the mixture is stirred at room temperature for 2 h. Another 4.82 ml of the tetrabutylammonium fluoride solution are then added, and the mixture is stirred at reflux temperature for another 3 h. The cooled reaction mixture is concentrated under reduced pressure and the residue is purified chromatographically on silica gel using n-heptane/ethyl acetate 2/1. This gives 4-[3-[3-(4-fluorophenyl)-3-hydroxypropyl]-2-(4-methoxyphenyl)-4-oxo-azetidin-1-yl]benzonitrile of molecular weight 430.48 ($C_{26}H_{23}FN_2O_3$); MS (ESI): 431.24 (M+H$^+$).

g) 1-(4-Aminomethylphenyl)-3-[3-(4-fluorophenyl)-3-hydroxypropyl]-4-(4-methoxy-phenyl)azetidin-2-one (42)

1.22 g of 4-[3-[3-(4-fluorophenyl)-3-hydroxypropyl]-2-(4-methoxyphenyl)-4-oxoazetidin-1-yl]benzonitrile are dissolved in 90 ml of ethanol, 10 ml of conc. ammonia solution and an excess of Raney nickel are added and the mixture is stirred at 60° C. and a hydrogen pressure of 10 bar for 8 h. Overnight, the reaction mixture cools to room temperature. The next day, the catalyst is separated off, the filtrate is concentrated under reduced pressure and the residue is purified chromatographically on silica gel using dichloromethane/methanol/ammonia solution 10/1/0.1. This gives 1-(4-aminomethylphenyl)-3-[3-(4-fluorophenyl)-3-hydroxypropyl]-4-(4-methoxyphenyl)azetidin-2-one of molecular weight 434.51 ($C_{26}H_{27}FN_2O_3$); MS (ESI): 418.2 (MH$^+$-NH$_3$).

h) Benzyl-(4-{4-[3-[3-(4-fluorophenyl)-3-hydroxypropyl]-2-(4-methoxyphenyl)-4-oxoazetidin-1-yl]benzylcarbamoyl}butyl)-(2,3,4,5,6-pentahydroxyhexyl)ammonium trifluoroacetate (35)

At room temperature, 100 mg of 5-[Benzyl-(2,3,4,5,6-pentahydroxyhexyl)amino]-pentanoic acid and 1.10 mg of 1-(4-aminomethylphenyl)-3-[3-(4-fluorophenyl)-3-hydroxypropyl]-4-(4-methoxyphenyl)azetidin-2-one are dissolved in 2 ml of dry dimethylformamide, 42 mg of N-hydroxybenzotriazole and 52 mg of 1-ethyl-3-(3-dimethylaminopropyl)carbodiimide hydrochloride are added and the mixture is stirred at room temperature overnight. The next day, the reaction mixture is concentrated under reduced pressure and, for purification, chromatographed on RP18 using acetonitrile/water with 0.1% trifluoroacetic acid. This gives benzyl-(4-{4-[3-[3-(4-fluorophenyl)-3-hydroxypropyl]-2-(4-methoxyphenyl)-4-oxoazetidin-1-yl]benzylcarbamoyl}butyl)-(2,3,4,5,6-pentahydroxyhexyl)ammonium trifluoroacetate of molecular weight 787.92 ($C_{44}H_{54}FN_3O_9$; cation); MS (ESI): 788.70 (M+H$^+$).

EXAMPLE XIX

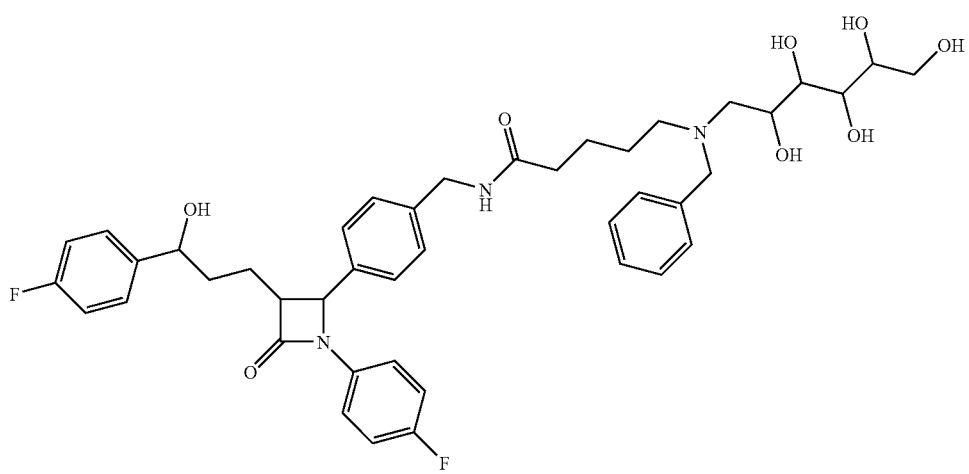

N-4-{1-(4-Fluorophenyl)-3-[3-(4-fluorophenyl)-3-hydroxypropyl]-4-oxoazetidin-2-yl}benzyl-5-[benzyl-(2,3,4,5,6-pentahydroxyhexyl)amino]pentanamide (43)

The compound of Example XIX is prepared starting from 5-[benzyl-(2,3,4,5,6-pentahydroxyhexyl)amino]pentanoic acid and 4-(4-aminomethylphenyl)-1-(4-fluorophenyl)-3-[3-(4-fluorophenyl)-3-hydroxypropyl]azetidin-2-one similarly to the compound of Example XVIII. This gives N-4-{1-(4-fluorophenyl)-3-[3-(4-fluorophenyl)-3-hydroxypropyl]-4-oxoazetidin-2-yl}benzyl-5-[benzyl-(2,3,4,5,6-pentahydroxyhexyl)amino]pentanamide of molecular weight 775.89 ($C_{43}H_{51}F_2N_3O_8$); MS (ESI): 776.4 (M+H$^+$).

EXAMPLE XX

N-{4-[3-[3-(4-Fluorophenyl)-3-hydroxypropyl]-2-(4-methoxyphenyl)-4-oxoazetidin-1-yl]benzyl}acetamide (44)

The compound of Example XX is prepared by reacting acetic acid similarly to Example XVIII with 1-(4-aminomethylphenyl)-3-[3-(4-fluorophenyl)-3-hydroxypropyl]-4-(4-methoxyphenyl)azetidin-2-one. This gives N-{4-[3-[3-(4-fluorophenyl)-3-hydroxypropyl]-2-(4-methoxyphenyl)-4-oxoazetidin-1-yl]benzyl}acetamide of molecular weight 476.55 ($C_{28}H_{29}FN_2O_4$); MS (ESI): 477.22 (M+H$^+$).

EXAMPLE XXI

5-(9H-Fluoren-9-ylmethoxycarbonylamino)-5-(4-{1-(4-fluorophenyl)-3-[3-(4-fluoro-phenyl)-3-hydroxypropyl]-4-oxoazetidin-2-yl}benzylcarbamoyl)pentyl]trimethyl-ammonium chloride (45)

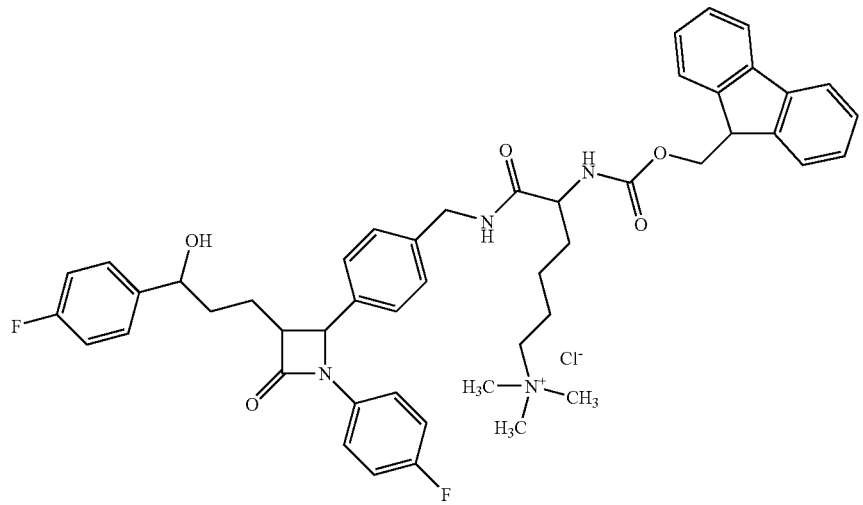

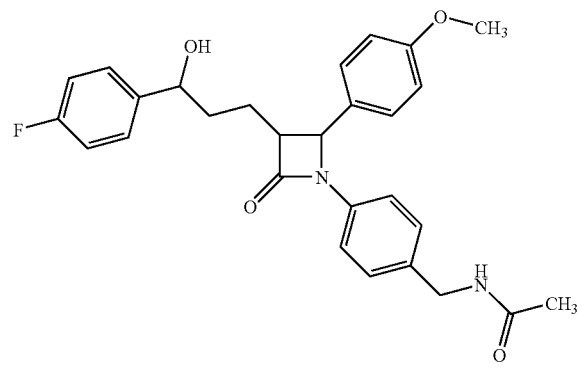

The compound of Example XXI is obtained similarly to the procedure of Example XIX by reacting 4-(4-aminomethylphenyl)-1-(4-fluorophenyl)-3-[3-(4-fluorophenyl)-3-hydroxypropyl]azetidin-2-one with [5-carboxy-5-(9H-fluoren-9-ylmethoxycarbonylamino)pentyl]trimethylammonium chloride. This gives [5-(9H-fluoren-9-ylmethoxycarbonylamino)-5-(4-{1-(4-fluorophenyl)-3-[3-(4-fluorophenyl)-3-hydroxypropyl]-4-oxoazetidin-2-yl}benzylcarbamoyl)pentyl]trimethylammonium chloride of molecular weight 815.99 ($C_{49}H_{53}F_2N_4O_5$; cation); MS (ESI): 815.81 (M+).

EXAMPLE XXII

[5-Amino-5-(4-{1-(4-fluorophenyl)-3-[3-(4-fluorophenyl)-3-hydroxypropyl]-4-oxoazetidin-2-yl}benzylcarbamoyl)pentyl]trimethylammonium chloride hydrochloride (46)

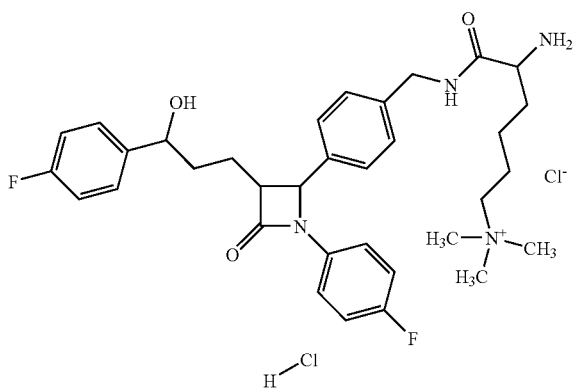

110 mg of the compound of Example XXI are dissolved in 2 ml of dry dimethylformamide, and 0.1 ml of piperidine are added. The reaction mixture is stirred at room temperature for 2 h and, after the reaction has ended, concentrated under reduced pressure. The residue is stirred in water, filtered off with suction and washed with water, and the filtrate is acidified with 2 N hydrochloric acid. The mixture is concentrated under reduced pressure and the residue is dried under high vacuum. The crude product is suspended in dichloromethane, the organic phase is decanted off and the residue is taken up in methanol, concentrated under reduced pressure and dried under high vacuum. This gives [5-amino-5-(4-{1-(4-fluorophenyl) 3-[3-(4-fluorophenyl)-3-hydroxypropyl]-4-oxoazetidin-2-yl}benzylcarbamoyl)-pentyl]trimethylammonium chloride hydrochloride of molecular weight 593.74 ($C_{34}H_{43}F_2N_4O_3$; cation); MS (ESI): 593.37 ($M^+$).

3-[2-[(4-Bromophenyl)-(4-fluorophenylamino)methyl]-5-(tert-butyldimethylsilanyloxy-5-(4-fluorophenyl)pentanoyl]-4-phenyloxazolidin-2-one (47)

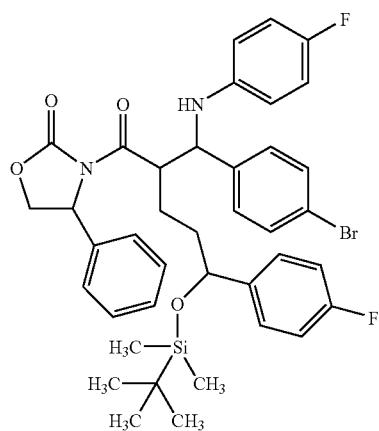

4.4 g of 3-[5-(tert-butyldimethylsilanyloxy)-5-(4-fluorophenyl)pentanoyl]-4-phenyloxazolidin-2-one are dissolved in 40 ml of absolute dichloromethane. 5.2 g of (4-bromobenzylidene)-(4-fluorophenyl)amine and 8.6 ml of ethyldiisopropylamine are added, and the solution is then cooled to −10° C. 2.94 ml of trimethylsilyl chloride are then added dropwise, and during the addition, the temperature of the reaction mixture is maintained below −5° C. The reaction solution is then stirred at −10° C. for half an hour and then cooled to −30° C., and 1.2 ml of titanium tetrachloride are added dropwise, the temperature being maintained between −30° C. and −15° C. This gives a black reaction solution which is stirred at −20° C. for another 3 h and then allowed to warm to 0° C. In the stated order, in intervals of 10 minutes, 10 ml of glacial acetic acid, 100 ml of 7% strength aqueous tartaric acid solution and finally 100 ml of 20% strength aqueous sodium hydrogensulfite solution are added with stirring. The mixture is then extracted twice with dichloromethane and the organic phase is washed once with saturated sodium chloride solution and dried over sodium sulfate. The solvent is removed using a rotary evaporator and the residue is purified by column chromatography ($SiO_2$; ethyl acetate/heptane 1:4). The product is obtained from diethyl ether/pentane as white crystals. $C_{39}H_{43}BrF_2N_2O_4Si$ (749) MS (ESI): $M^+$ 4-(4-Bromophenyl)-3-[3-(tert-butyldimethylsilanyloxy)-3-(4-fluorophenyl)propyl]-1-(4-fluorophenyl) azetidin-2-one (48)

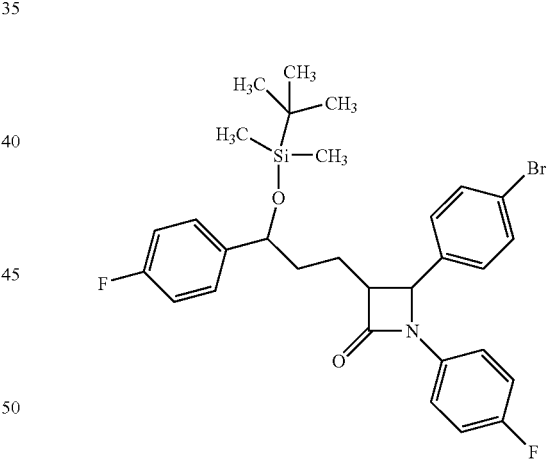

3.34 g of 3-[2-[(4-bromophenyl)-(4-fluorophenylamino)methyl]-5-(tert-butyl-dimethylsilanyloxy)-5-(4-fluorophenyl)pentanoyl]-4-phenyloxazolidin-2-one are suspended in 70 ml of tert-butyl methyl ether. 3.8 ml of bis(trimethylsilyl)acetamide and 144 mg of tributylammonium fluoride trihydrate are then added. The reaction mixture is stirred at room temperature overnight, and 0.7 ml of glacial acetic acid are then added. The reaction mixture is concentrated using a rotary evaporator and the residue is purified by column chromatography ($SiO_2$; ethyl acetate/heptane 1:4). The product is, obtained as a clear oil. $C_{30}H_{34}BrF_2NO_2Si$ (586) MS (ESI): $M^+$-131

3-{5-(tert-Butyldimethylsilanyloxy)-5-(4-fluorophenyl)-2-[(4-fluorophenylamino)-(4-hydroxyphenyl)methyl]pentanoyl}-4-phenyloxazolidin-2-one (49)

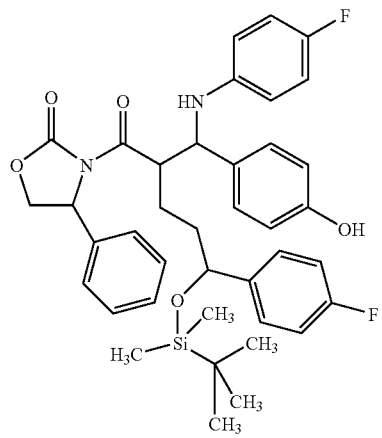

10 g of 3-[5-(tert-butyldimethylsilanyloxy)-5-(4-fluorophenyl)pentanoyl]-4-phenyloxazolidin-2-one are dissolved in 80 ml of absolute dichlormethane. 9.12 g of 4-[(4-fluorophenylimino)methyl]phenol and 19.6 ml of ethyldiisopropylamine are added, and the solution is then cooled to −10° C. 6.7 ml of trimethylsilyl chloride are then added dropwise, the temperature of the reaction mixture being maintained at below −5° C. The reaction solution is stirred at −10° C. for half an hour and then cooled to −30° C., and 2.7 ml of titanium tetrachloride are added dropwise, the temperature being maintained between −30° C. and −15° C. This gives a black reaction solution which is stirred at −20° C. for another 3 h and then allowed to warm to 0° C. In the stated order, in intervals of 10 minutes, 6 ml of glacial acetic acid, 60 ml of 7% strength aqueous tartaric acid solution and finally 100 ml of 20% strength aqueous sodium hydrogensulfite solution are then added with stirring. The mixture is then extracted three times with dichloromethane and the organic phase is washed once with saturated sodium chloride solution and dried over sodium sulfate. The solvent is removed using a rotary evaporator and the residue is purified by column chromatography (SiO$_2$; ethyl acetate/heptane 1:4). The product is obtained from diethyl ether/pentane as white crystals. C$_{39}$H$_{44}$F$_2$N$_2$O$_5$Si (686) MS (ESI): M$^+$-241

3-[3-(tert-Butyldimethylsilanyloxy)-3-(4-fluorophenyl)propyl]-1-(4-fluorophenyl)-4-(4 hydroxyphenyl)azetidin-2-one (50)

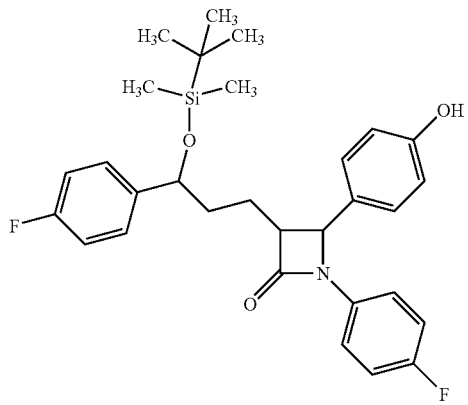

2.63 g of 3-{5-(tert-butyldimethylsilanyloxy)-5-(4-fluorophenyl)-2-[(4-fluorophenyl amino)-(4-hydroxyphenyl)methyl]pentanoyl}-4-phenyloxazolidin-2-one are suspended in 60 ml of tert-butyl methyl ether. 3.22 ml of bis(trimethylsilyl)acetamide and 122 mg of tributylammonium fluoride trihydrate are then added. The reaction mixture is stirred at room temperature for 3 h, and 0.6 ml of glacial acetic acid are then added. The reaction mixture is concentrated using a rotary evaporator and the residue is purified by column chromatography (SiO$_2$; ethyl acetate/heptane 1:4). The product is obtained as clear crystals. C$_{30}$H$_{35}$F$_2$NO$_3$Si (523) MS (ESI): M$^+$-131

[3-(4-{1-(4-Fluorophenyl)-3-[3-(4-fluorophenyl)-3-hydroxypropyl]-4-oxoazetidin-2-yl}phenoxy)propyl]trimethylammonium bromide (51)

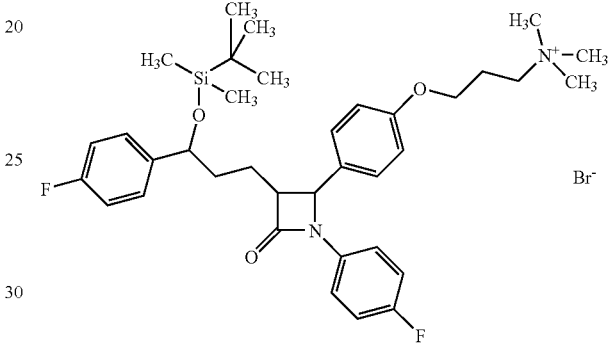

210 mg of 3-[3-(tert-butyldimethylsilanyloxy)-3-(4-fluorophenyl)propyl]-1-(4-fluorophenyl)-4-(4-hydroxyphenyl)azetidin-2-one are dissolved in 4 ml of absolute acetonitrile. 170 mg of KF-alumina (1.15 mol/100) and 200 mg of (3-bromopropyl) trimethylammonium bromide are then added. The reaction mixture is stirred at room temperature for 4 h and then filtered. The mother liquor is concentrated using a rotary evaporator and the residue is purified using a 5 g SiO$_2$ cartridge (dichloromethane/methanol 5:1). The product is obtained as an oil.
C$_{36}$H$_{49}$BrF$_2$N$_2$O$_3$Si (703) MS (ESI): M$^+$-80

EXAMPLE XXIII

[3-(4-{1-(4-Fluorophenyl)-3-[3-(4-fluorophenyl)-3-hydroxypropyl]-4-oxoazetidin-2-yl}phenoxy)propyl]trimethylammonium bromide (52)

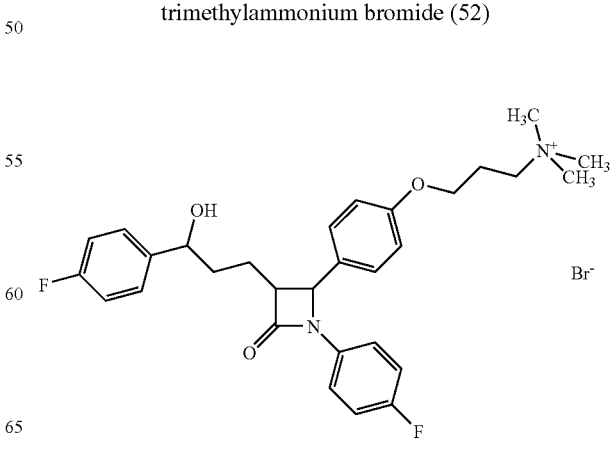

180 mg of (3-{4-[3-[3-(tert-butyldimethylsilanyloxy)-3-(4-fluorophenyl)propyl]-1-(4-fluorophenyl)-4-oxoazetidin-2-yl]phenoxy}propyl)trimethylammonium bromide are dissolved in 10 ml of methanol. 1 ml of a 0.1 M aqueous HCl solution is then added, and the reaction solution is stirred at room temperature overnight. The mixture is neutralized with dilute aqueous sodium bicarbonate solution and concentrated using a rotary evaporator. The residue is purified using a 10 g SiO$_2$ cartridge (dichloromethane/methanol 5:1). The product is obtained as a hygroscopic solid. C$_{30}$H$_{35}$BrF$_2$N$_2$O$_3$ (589) MS (ESI): M$^+$-80

[5-(4-{1-(4-Fluorophenyl)-3-[3-(4-fluorophenyl)-3-(tert-butyldimethylsilanyloxy)propyl]-4-oxoazetidin-2-yl}phenoxy)pentyl]trimethylammonium bromide (53)

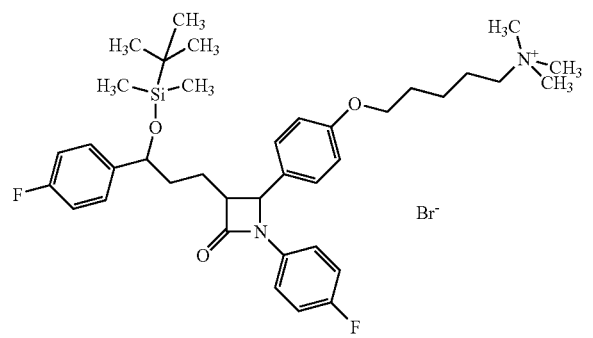

370 mg of 3-[3-(tert-butyldimethylsilanyloxy)-3-(4-fluorophenyl)propyl]-1-(4-fluorophenyl)-4-(4-hydroxyphenyl)azetidin-2-one are dissolved in 3 ml of absolute acetonitrile. 300 mg of KF-alumina (1.15 mol/100 g) and 375 mg of (3-bromopentyl)-trimethylammonium bromide are then added. The reaction mixture is stirred at room temperature overnight and then filtered. The mother liquor is concentrated using a rotary evaporator and the residue is purified using a 5 g SiO$_2$ cartridge (dichloromethane/methanol 4:1). The product is obtained as an oil.
C$_{38}$H$_{53}$BrF$_2$NO$_3$Si (731) MS (ESI): M$^+$-80

EXAMPLE XXIV

[5-(4-{1-(4-Fluorophenyl)-3-[3-(4-fluorophenyl)-3-hydroxypropyl]-4-oxoazetidin-2-yl}phenoxy)pentyl]trimethylammonium bromide (54)

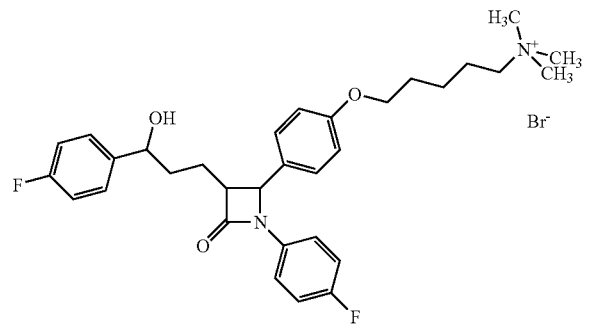

548 mg of [5-(4-{1-(4-fluorophenyl)-3-[3-(4-fluorophenyl)-3-(isopropyldimethyl-silanyloxy)propyl]-4-oxoazetidin-2-yl}phenoxy)pentyl]trimethylammonium bromide are dissolved in 20 ml of methanol. 1 ml of a 0.1 M aqueous HCl solution is then added, and the reaction solution is stirred at room temperature overnight. The mixture is neutralized with dilute aqueous sodium bicarbonate solution and concentrated using a rotary evaporator. The residue is purified using a 10 g SiO$_2$ cartridge (dichloromethane/methanol 5:1). The product is obtained as a hygroscopic solid. C$_{32}$H$_{39}$BrF$_2$N$_2$O$_3$ (617) MS (ESI): M$^+$-80

1-(4-Fluorophenyl)-3-[3-(4-fluorophenyl)-3-hydroxypropyl]-4-[4-(4-iodobutoxy)phenyl]azetidin-2-one (55)

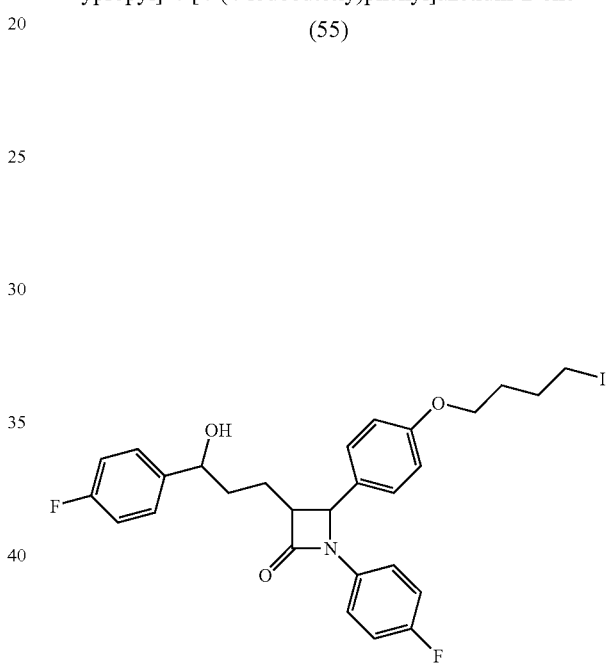

100 mg of 1-(4-fluorophenyl)-3-[3-(4-fluorophenyl)-3-hydroxypropyl]-4-(4-hydroxy-phenyl)azetidin-2-one are dissolved in 10 ml of absolute dimethylformamide. 80 mg of powdered potassium carbonate and 0.2 ml of diiodobutane are then added. The reaction solution is stirred at room temperature overnight. Following concentration using a rotary evaporator and oil pump vacuum at 40° C., the residue is purified using an SiO$_2$ cartridge (n-heptane; n-heptane/ethyl acetate 4:1). The product is obtained as an oil. C$_{28}$H$_{28}$F$_2$INO$_3$ (591) MS (ESI): M$^+$-18

EXAMPLE XXV 1-(4-Fluorophenyl)-3-[3-(4-fluorophenyl)-3-hydroxypropyl]-4-(4-{4-[methyl-(2,3,4,5,6-pentahydroxyhexyl)amino]butoxy}phenyl)azetidin-2-one (56)

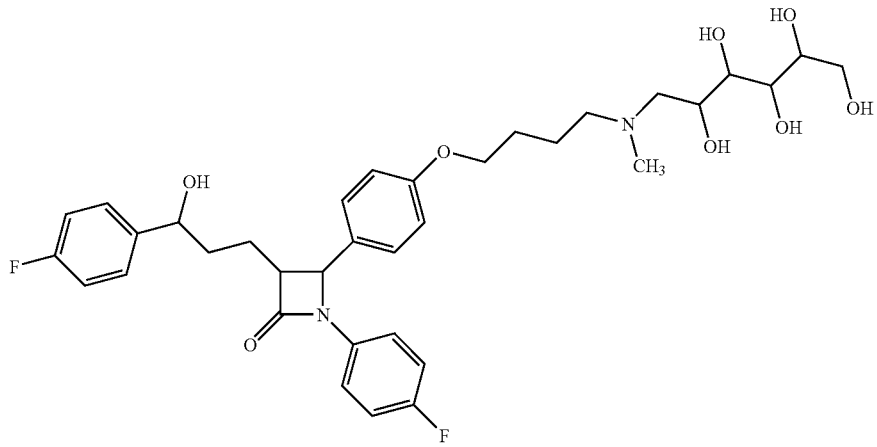

100 mg of 1'-(4-fluorophenyl)-3-[3-(4-fluorophenyl)-3-hydroxypropyl]-4-[4-(4-iodobutoxy)phenyl]azetidin-2-one are dissolved in 5 ml of absolute dimethylformamide. 132 mg of 6-methylaminohexane-1,2,3,4,5-pentaol are then added, and the reaction solution is stirred at 50° C. for 2 h. After concentration using a rotary evaporator and oil pump vacuum at 40° C., the residue is purified by preparative HPLC. The product (89 mg) is obtained as an oil. $C_{35}H_{44}F_2N_2O_8$ (658) MS (ESI): M+

1-(4-Fluorophenyl)-3-[3-(4-fluorophenyl)-3-hydroxypropyl]-4-[4-(5-iodopentyloxy)-phenyl]azetidin-2-one (57)

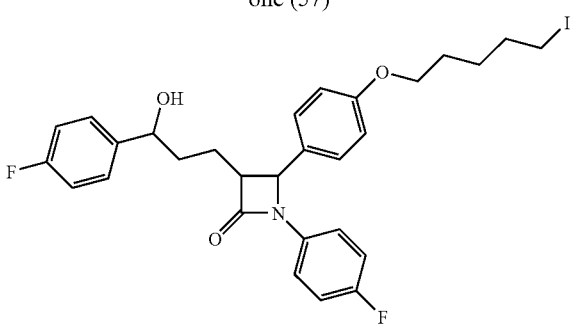

150 mg of 1-(4-fluorophenyl)-3-[3-(4-fluorophenyl)-3-hydroxypropyl]-4-(4-hydroxyphenyl)azetidin-2-one are dissolved in 10 ml of absolute dimethylformamide. 120 mg of powdered potassium carbonate and 0.33 ml of diiodopentane are then added. The reaction solution is stirred at room temperature overnight. After concentration using a rotary evaporator and oil pump vacuum at 40° C., the residue is purified using an $SiO_2$ cartridge (n-heptane; n-heptane/ethyl acetate 4:1). The product is obtained as an oil. $C_{29}H_{30}F_2INO_3$ (605) MS (ESI): M+-18

EXAMPLE XXVI 1-(4-Fluorophenyl)-3-[3-(4-fluorophenyl)-3-hydroxypropyl]-4-(4-{5-[methyl-(2,3,4,5,6-pentahydroxyhexyl)amino]pentyloxy}phenyl)azetidin-2-one (58)

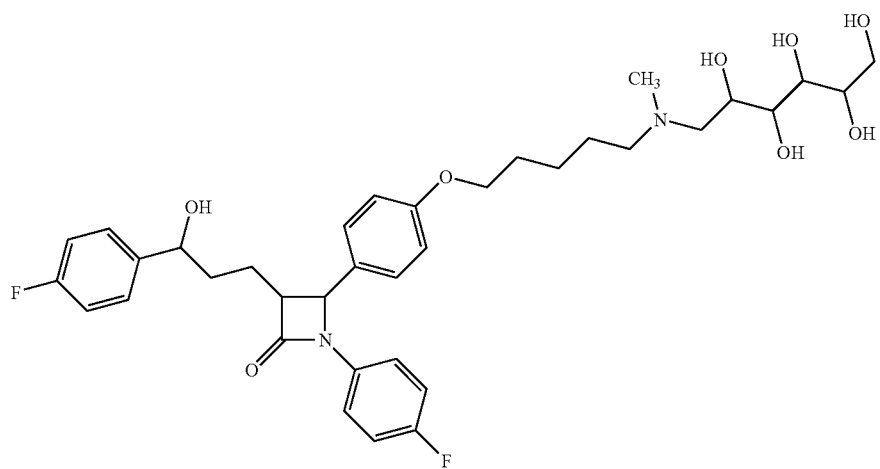

170 mg of 1-(4-fluorophenyl)-3-[3-(4-fluorophenyl)-3-hydroxypropyl]-4-[4-(5-iodopentyloxy)phenyl]azetidin-2-one are dissolved in 5 ml of absolute dimethylformamide. 220 mg of 6-methylaminohexane-1,2,3,4,5-pentaol are then added, and the reaction solution is stirred at 50° C. for 2 h. After concentration using a rotary evaporator and oil pump vacuum at 40° C., the residue is purified by preparative HPLC. The product is obtained as an oil. $C_{36}H_{46}F_2N_2O_8$ (672) MS (ESI): $M^+$ 1-(4-Fluorophenyl)-3-[3-(4-fluorophenyl)-3-hydroxypropyl]-4-[4-(6-iodohexyloxy)-phenyl]azetidin-2-one (59)

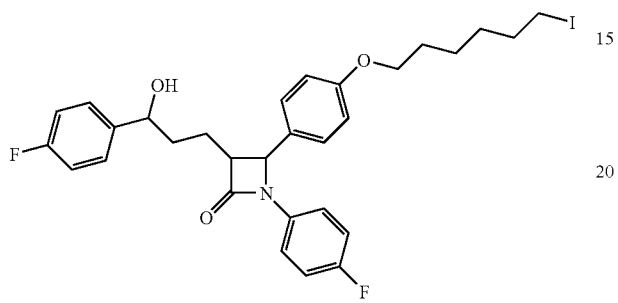

100 mg of 1-(4-fluorophenyl)-3-[3-(4-fluorophenyl)-3-hydroxypropyl]-4-(4 hydroxyphenyl)azetidin-2-one are dissolved in 10 ml of absolute dimethylformamide. 80 mg of powdered potassium carbonate and 0.25 ml of diiodohexane are then added. The reaction solution is stirred at room temperature overnight. After concentration using a rotary evaporator and oil pump vacuum at 40° C., the residue is purified using an $SiO_2$ cartridge (n-heptene; n-heptane/ethyl acetate 4:1). The product is obtained as an oil. $C_{30}H_{32}F_2INO_3$ (619) MS (ESI): $M^+$-18

EXAMPLE XXVII 1-(4-Fluorophenyl)-3-[3-(4-fluorophenyl)-3-hydroxypropyl]-4-(4-{6-[methyl-(2,3,4,5,6-pentahydroxyhexyl)amino]hexyloxy}phenyl)azetidin-2-one (60)

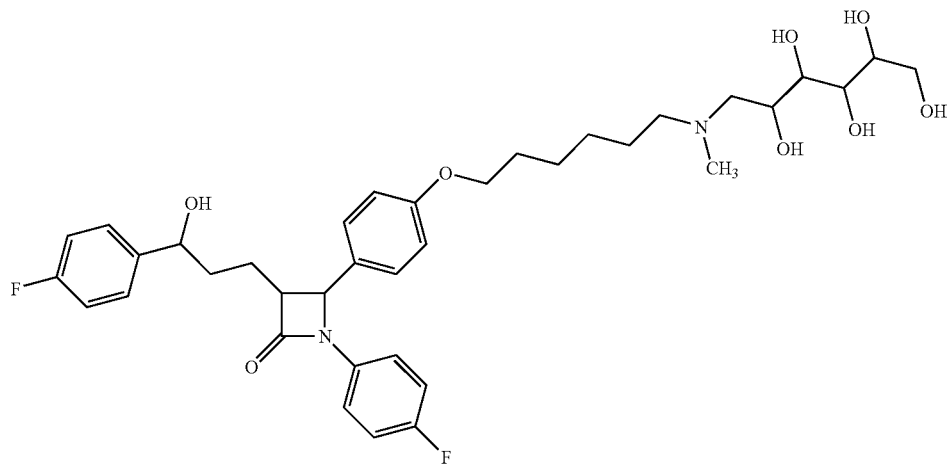

136 mg of 1-(4-fluorophenyl)-3-[3-(4-fluorophenyl)-3-hydroxypropyl]-4-[4-(6-iodohexyloxy)phenyl]azetidin-2-one are dissolved in 10 ml of absolute dimethylformamide. 172 mg of 6-methylaminohexane-1,2,3,4,5-pentaol are then added, and the reaction solution is stirred at 50° C. for 2.5 h. After concentration using a rotary evaporator and oil pump vacuum at 40° C., the residue is purified by preparative HPLC. The product is obtained as an oil. $C_{37}H_{48}F_2N_2O_8$ (686) MS (ESI): $M^+$ 1-(4-Fluorophenyl)-3-[3-(4-fluorophenyl)-3-hydroxypropyl]-4-[4-(8-iodooctyloxy)-phenyl]azetidin-2-one (61)

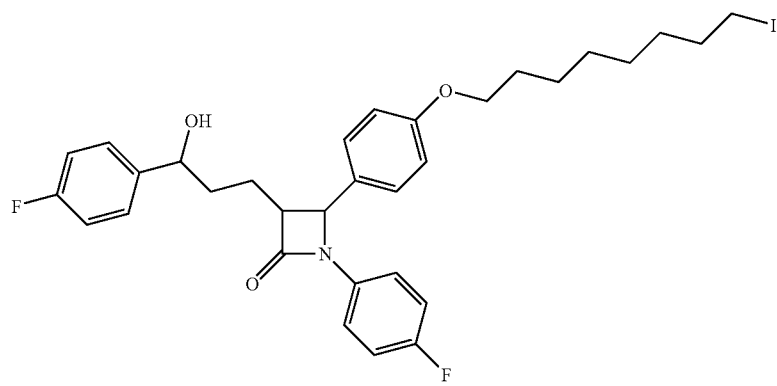

150 mg of 1-(4-fluorophenyl)-3-[3-(4-fluorophenyl)-3-hydroxypropyl]-4-(4-hydroxyphenyl)azetidin-2-one are dissolved in 10 ml of absolute dimethylformamide. 120 mg of powdered potassium carbonate and 0.44 ml of diiodooctane are then added. The reaction solution is stirred at room temperature overnight. After concentration using a rotary evaporator and oil pump vacuum at 40° C., the residue is purified using an $SiO_2$ cartridge (n-heptane; n-heptane/ethylacetate 4:1). The product is obtained as an oil. $C_{32}H_{36}F_2INO_3$ (647) MS (ESI): $M^+$-18

EXAMPLE XXVIII 1-(4-Fluorophenyl)-3-[3-(4-fluorophenyl)-3-hydroxypropyl]-4-(4-{8-[methyl-(2,3,4,5,6-pentahydroxyhexyl)amino]octyloxy}phenyl)azetidin-2-one (62)

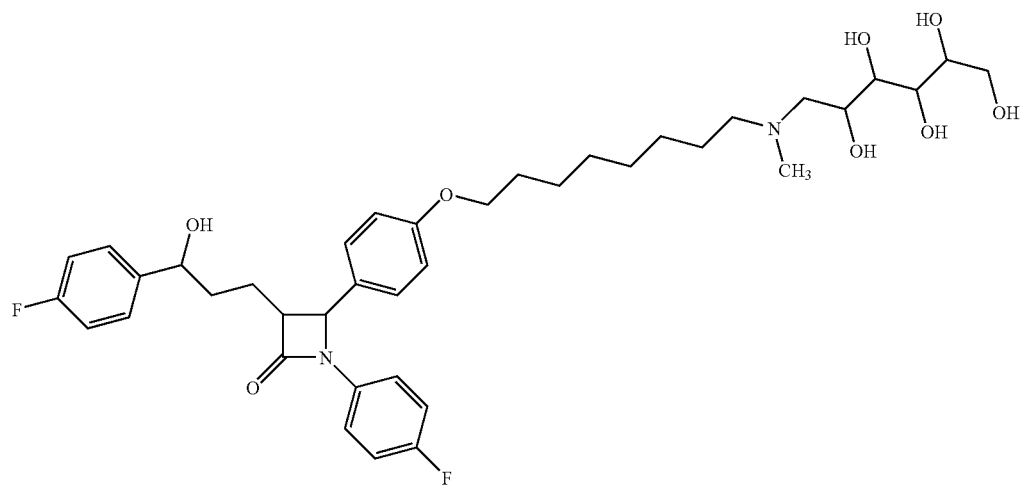

150 mg of 1-(4-fluorophenyl)-3-[3-(4-fluorophenyl)-3-hydroxypropyl]-4-[4-(8-iodooctyloxy)phenyl]azetidin-2-one are dissolved in 5 ml of absolute dimethylformamide. 180 mg of 6-methylaminohexane-1,2,3,4,5-pentaol are then added, and the reaction solution is stirred at 50° C. for 2 h. After concentration using a rotary evaporator and oil pump vacuum at 40° C., the residue is purified by preparative HPLC. The product is obtained as an oil. $C_{39}H_{52}F_2N_2O_8$ (714) MS (ESI): $M^+$ 1-(4-Fluorophenyl)-3-[3-(4-fluorophenyl)-3-hydroxypropyl]-4-[4-(10-iododecyloxy)-phenyl]azetidin-2-one (63)

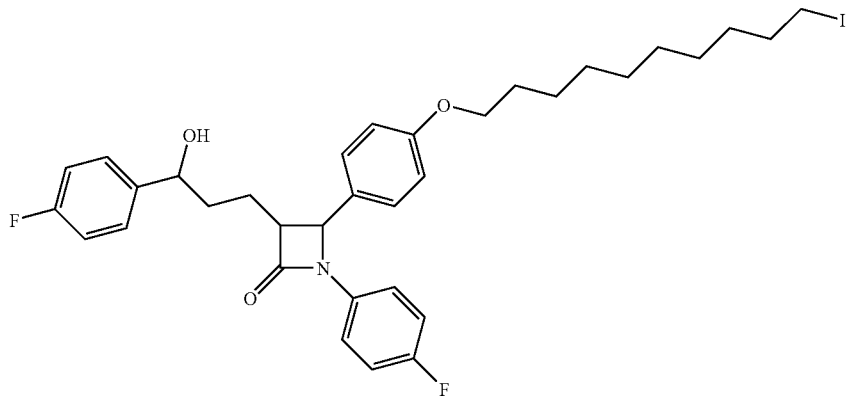

150 mg of 1-(4-fluorophenyl)-3-[3-(4-fluorophenyl)-3-hydroxypropyl]-4-(4 hydroxyphenyl)azetidin-2-one are dissolved in 10 ml of absolute dimethylformamide. 120 mg of powdered potassium carbonate and 865 mg of diiododecane are then added. The reaction solution is stirred at room temperature overnight. After concentration using a rotary evaporator and oil pump vacuum at 40° C., the residue is purified using an SiO₂ cartridge (n-heptane; n-heptane/ethyl acetate- 4:1). The product is obtained as an oil. $C_{34}H_{40}F_2INO_3$ (675) MS (ESI): M⁺-18

EXAMPLE XXIX 1-(4-Fluorophenyl)-3-[3-(4-fluorophenyl)-3-hydroxypropyl]-4-(4-{10-[methyl-(2,3,4,5,6-pentahydroxyhexyl)amino]decyloxy}phenyl)azetidin-2-one (64)

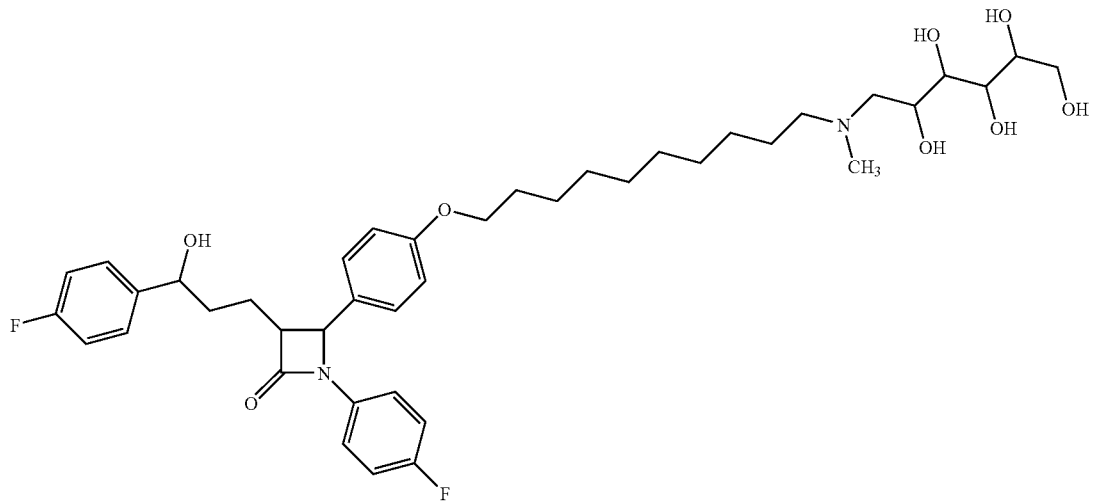

170 mg of 1-(4-fluorophenyl)-3-[3-(4-fluorophenyl)-3-hydroxypropyl]-4-[4-(10-iododecyloxy)phenyl]azetidin-2-one are dissolved in 5 ml of absolute dimethylformamide. 200 mg of 6-methylaminohexane-1,2,3,4,5-pentaol are then added, and the reaction solution is stirred at 50° C. for 2 h. After concentration using a rotary evaporator and oil pump pressure at 40° C., the residue is purified by preparative HPLC. The product is obtained as an oil. $C_{41}H_{56}F_2N_2O_8$ (742) MS (ESI): M⁺

1-(4-Fluorophenyl)-3-[3-(4-fluorophenyl)-3-hydroxypropyl]-4-(4-{2-[2-(2-iodoethoxy)ethoxy]ethoxy}phenyl)azetidin-2-one (5)

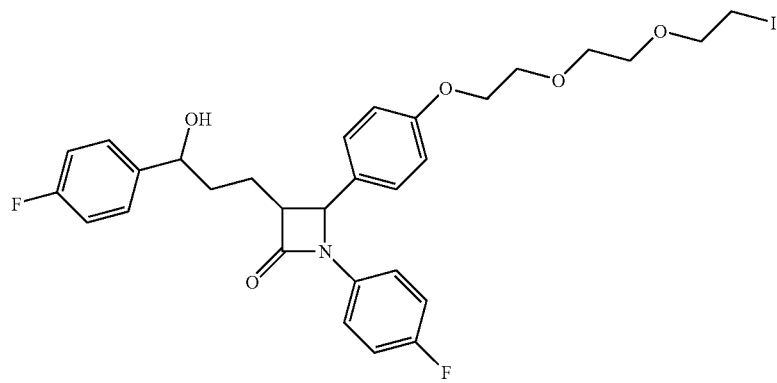

150 mg of 1-(4-fluorophenyl)-3-[3-(4-fluorophenyl)-3-hydroxypropyl]-4-(4 hydroxyphenyl)azetidin-2-one are dissolved in 10 ml of absolute dimethylformamide. 120 mg of powdered potassium carbonate and 0.4 ml of 1,2-bis(diiodoethoxy)ethane are then added. The reaction solution is stirred at room temperature overnight. After concentration using a rotary evaporator and oil pump vacuum at 40° C., the residue is purified using an $SiO_2$ cartridge (n-heptane; n-heptane/ethylacetate 4:1). The product is obtained as an oil. $C_{30}H_{32}F_2INO_5$ (651) MS (ESI): $M^+$-18

EXAMPLE XXX 1-(4-Fluorophenyl)-3-[3-(4-fluorophenyl)-3-hydroxypropyl]-4-{4-[2-(2-{2-[methyl-(2,3,4,5,6-pentahydroxyhexyl)amino]ethoxy}ethoxy)ethoxy]phenyl}azetidin-2-one (66)

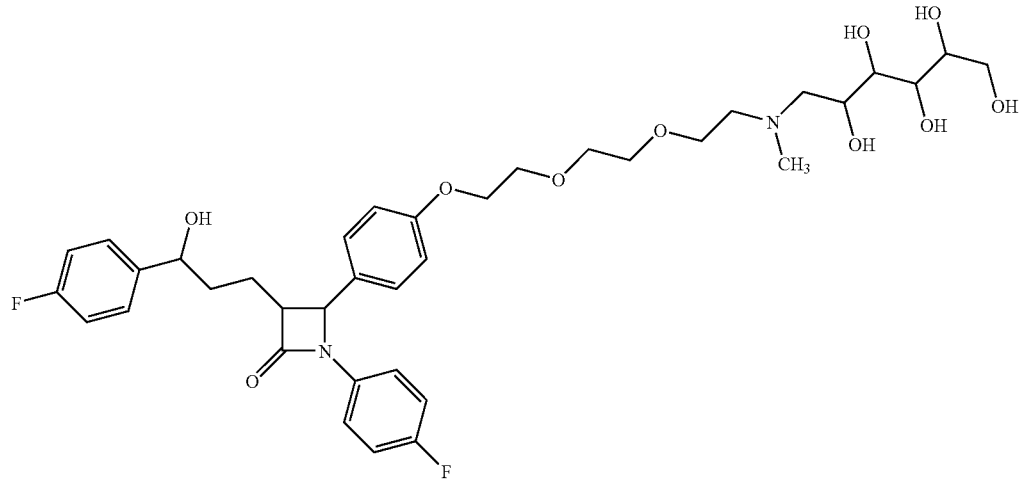

230 mg of 1-(4-fluorophenyl)-3-[3-(4-fluorophenyl)-3-hydroxypropyl]-4-(4-{2-[2-(2-iodoethoxy)ethoxy]ethoxy}phenyl)azetidin-2-one are dissolved in 5 ml of absolute dimethylformamide. 280 mg of 6-methylaminohexane-1,2,3,4,5-pentaol are then added, and the reaction solution is stirred at 50° C. for 2 h. After concentration using a rotary evaporator and oil pump vacuum at 40° C., the residue is purified by preparative HPLC. The product is obtained as an oil. $C_{37}H_{48}F_2N_2O_{10}$ (718) MS (ESI): $M^+$ N-methyl-N-(2,3,4,5,6-pentahydroxyhexyl)hex-5-enamide (67)

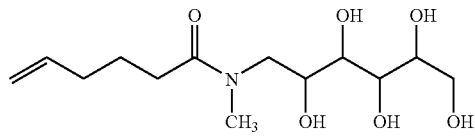

1.11 g of 5-hexenoic acid are dissolved in 3 ml of absolute methylene dichloride. 1.4 ml of thionyl chloride are then added dropwise. The mixture is stirred at room temperature for 3 h and then concentrated using a rotary evaporator. 1.09 g of 6-methylaminohexane-1,2,3,4,5-pentaol are suspended in 5 ml of absolute methylene dichloride. 5-hexenoic chloride dissolved in 3 ml of absolute methylene dichloride is added dropwise, and the mixture is then stirred at room temperature for 4 h. The resulting precipitate is filtered off from the reaction product, the filtrate is concentrated using a rotary evaporator and the oily crude product is reacted further without any purification. $C_{13}H_{25}NO_6$ (291) MS (ESI): $M^+$ N-methyl-N-(2,3,4,5,6-pentahydroxyhexyl)-6-{4-[3-[3-(tert-butyldimethylsilanyloxy)-3-(4-fluorophenyl)propyl]-1-(4-fluorophenyl)-4-oxoazetidin-2-yl]phenyl}hex-5-enamide (68)

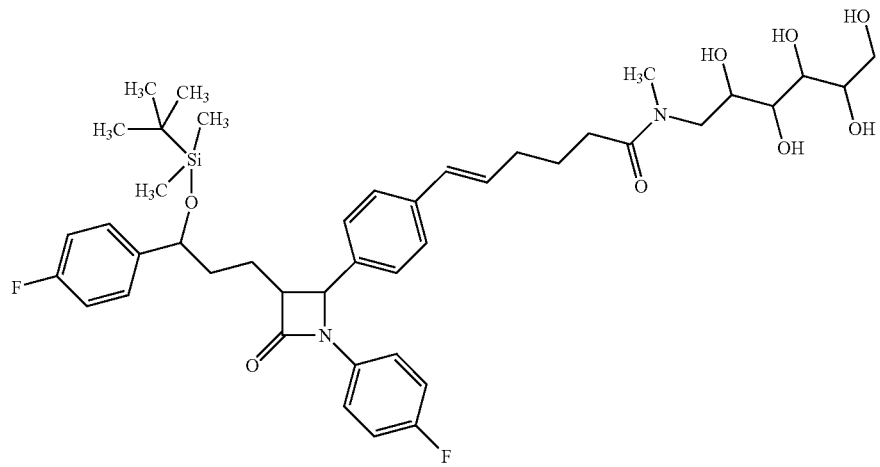

110 mg of 4-(4-bromophenyl)-3-[3-(tert-butyldimethylsilanyloxy)-3-(4-fluorophenyl)propyl]-1-(4-fluorophenyl)azetidin-2-one and 136 mg of N-methyl-N-(2,3,4,5,6-pentahydroxyhexyl)hex-5-enamide are initially charged in 300 µl of triethylamine under argon in a closed tube which had been heated thoroughly beforehand. After addition of 6 mg of palladium acetate and 14 mg of triphenylphosphine, the mixture is stirred at 100° C. for 4 h. The reaction mixture is then taken up in dichloromethane, filtered and concentrated using a rotary evaporator. Purification of the residue using an $SiO_2$ cartridge (dichloromethane/methanol 20:1-5:1) gives the product. $C_{43}H_{58}F_2N_2O_8Si$ (796)

EXAMPLE XXXI

N-methyl-N-(2,3,4,5,6-pentahydroxyhexyl)-6-(4-{1-(4-fluorophenyl)-3-[3-(4-fluorophenyl)-3-hydroxypropyl]-4-oxoazetidin-2-yl}phenyl)hex-5-enamide (69)

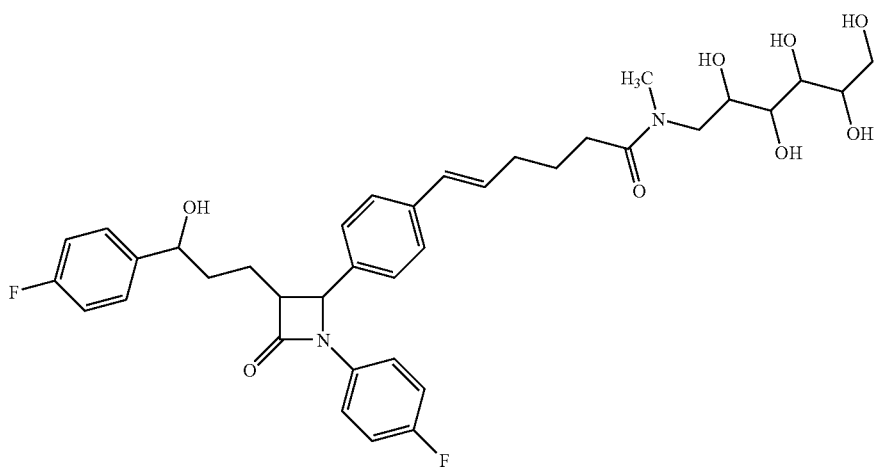

70 mg of N-methyl-N-(2,3,4,5,6-pentahydroxyhexyl)-6-{4-[3-[3-(tert-butyldimethylsilanyloxy)-3-(4-fluorophenyl)propyl]-1-(4-fluorophenyl)-4-oxoazetidin-2-yl]phenyl}hex-5-enamide are dissolved in 6 ml of methanol. 0.1 N $HCl_{(aq)}$ is then added, and the mixture is stirred at room temperature overnight. The mixture is then neutralized with 1 N aqueous sodium hydroxide solution and concentrated using a rotary evaporator. The residue is stirred with dichloromethane and filtered and the mother liquor is concentrated using a rotary evaporator. The product is obtained following purification by preparative HPLC: $C_{31}H_{44}F_2N_2O_8$ (682) MS (ESI): $M^+$-18

EXAMPLE XXXII

2-{[4-(4-{1-(4-Fluorophenyl)-3-[3-(4-fluorophenyl)-3-hydroxypropyl]-4-oxoazetidin-2-yl}phenoxy)butyl]methylamino}ethanesulfonic acid (70)

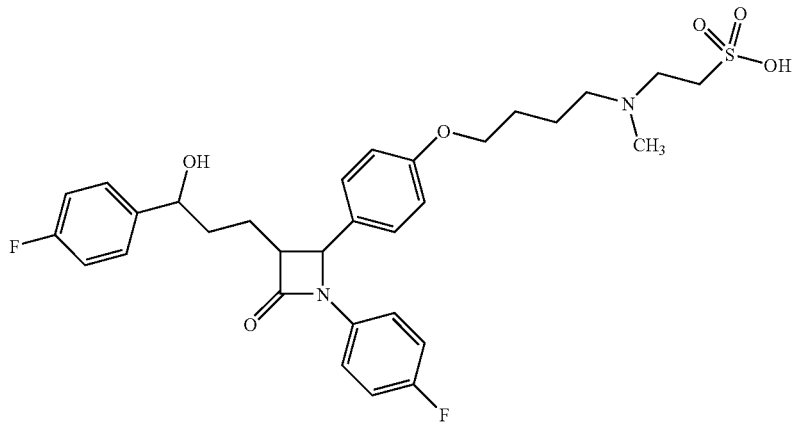

64.5 mg of 1-(4-fluorophenyl)-3-[3-(4-fluorophenyl)-3-hydroxypropyl]-4-[4-(4 iodobutoxy)phenyl]azetidin-2-one are dissolved in 3 ml of methanol. 60.7 mg of 2-methylaminoethanesulfonic acid are then dissolved in 1 ml of water, and 30.4 mg of potassium carbonate are added. The reaction solution is stirred at 50° C. for 8 h. After concentration using a rotary evaporator at 40° C., the residue is passed over a reverse-phase cartridge (methanol). The resulting crude product is dissolved in hot methanol. The precipitate formed on cooling is filtered off, and the mother liquor is concentrated using a rotary evaporator. The product is obtained as an oil.

$C_{31}H_{36}F_2N_2O_6S$ (602) MS (ESI): $M^+$-18

EXAMPLE XXXIII 1-(4-Fluorophenyl)-3-[1-(4-fluorophenyl)-2-oxo-4-(4-sulfoxyphenyl)azetidin-3-yl]propyl acetate (71)

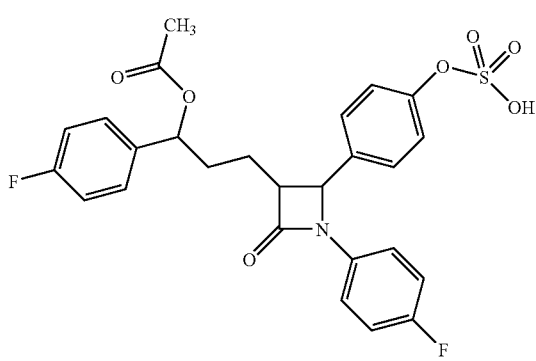

64.5 mg of 1-(4-fluorophenyl)-3-[3-(4-fluorophenyl)-3-hydroxypropyl]-4-[4-(4 iodobutoxy)phenyl]azetidin-2-one are dissolved in 3 ml of methanol. 60.7 mg of 2-methylaminoethanesulfonic acid are then dissolved in 1 ml of water, and 30.4 mg of potassium carbonate are added. The reaction solution is stirred at 50° C. for 8 h. After concentration using a rotary evaporator at 40° C., the residue is passed over a reverse-phase cartridge (methanol). The resulting crude product is dissolved in hot methanol. The precipitate formed on cooling is filtered off, and the mother liquor is concentrated using a rotary evaporator. The product is obtained as an oil.

$C_{31}H_{36}F_2N_2O_6S$ (602) MS (ESI): $M^+$-18

EXAMPLE XXXIII 1-(4-Fluorophenyl)-3-[1-(4-fluorophenyl)-2-oxo-4-(4-sulfoxyphenyl)azetidin-3-yl]propyl acetate (71)

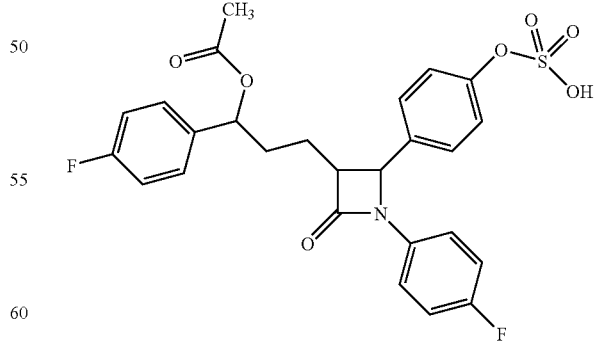

$C_{24}H_{21}F_2NO_6S$ (489.50) MS (ESI): $M^+$=490.2.

EXAMPLE XXXV 2,3,4,5-Tetraacetoxy-1-{3-[3-[3-(4-fluorophenyl)-hydroxypropyl]-2-(4-methoxyphenyl)-4-oxoazetidin-1-yl]benzylcarbamoyl}pentyl acetate (73)

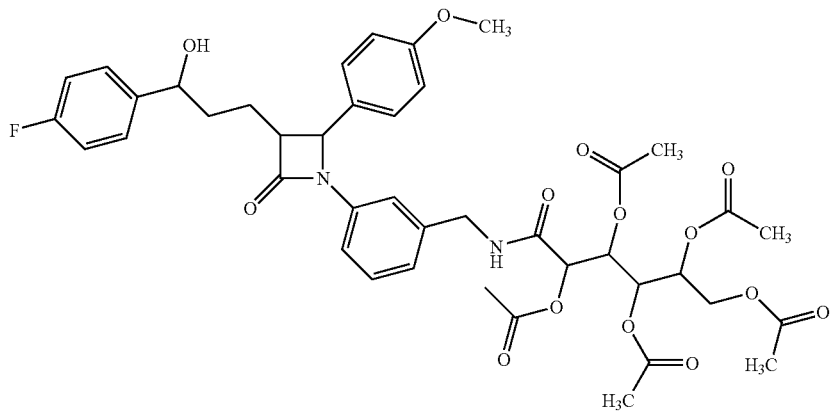

112 mg (0.24 mmol) of 1-(3-aminomethylphenyl)-3-[3-(4-fluorophenyl)-3-hydroxypropyl]4-(4-methoxyphenyl)azetidin-2-one are dissolved in 5 ml of methylene chloride and 0.5 ml of triethylamine. At 0° C., 0.5 g of 2,3,4-triacetoxy-1-(acetoxychlorocarbonylmethyl)butyl acetate are added, and the mixture is allowed to thaw to room temperature. After 30 minutes, the mixture is diluted with ethyl acetate and then filtered through silica gel. The solvent is distilled off and the residue is purified by flash chromatography. The product is obtained as an amorphous solid:

$C_{42}H_{47}FN_2O_{14}$ (822.84) MS (ESI): $M^+$=823.3.

EXAMPLE XXXVI

N-3-[3-[3-(4-Fluorophenyl)-3-hydroxypropyl]-2-(4-methoxyphenyl)-4-oxoazetidin-1-yl]benzyl-2,3,4,5,6-pentahydroxyhexanamide (74)

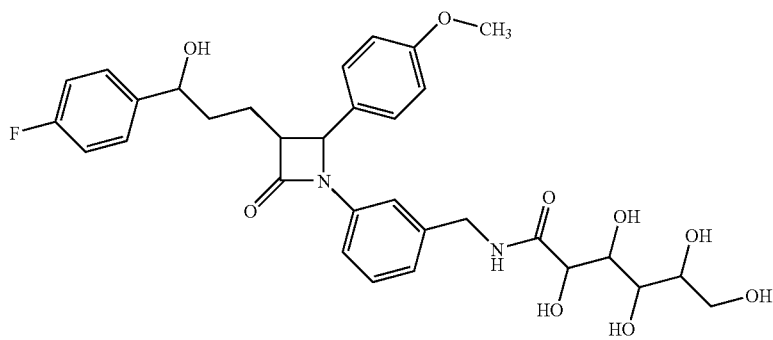

90 mg-(109 μmol) of 2,3,4,5-tetraacetoxy-1-{3-[3-[3-(4-fluorophenyl)-3-hydroxy-propyl]-2-(4-methoxyphenyl-4-oxoazetidin-1-yl]benzylcarbamoyl}pentyl acetate are dissolved in 7 ml of methanol and 0.5 ml of 1 N NaOMe/MeOH is added. After 2 hours at room temperature the mixture is neutralized with methanolic hydrochloric acid and concentrated. The residue is purified by flash chromatography. The product is obtained as an amorphous solid. $C_{32}H_{37}FN_2O_9$ (612.66) MS (ESI): $M^+$=613.2.

EXAMPLE XXXVII

N-Methyl-N-(2,3,4,5,6-pentahydroxyhexyl)-6-(4-{3-[1-(4-fluorophenyl)-2-(4-methoxy-phenyl)-4-oxoazetidin-3-yl]-1-hydroxypropyl}phenyl)hex-5-enamide (75)

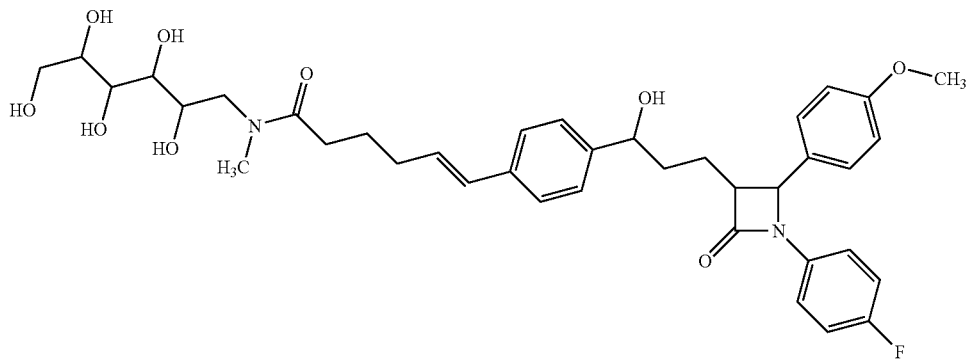

200 mg of N-methyl-N-(2,3,4,5,6-pentahydroxyhexyl) hex-5-enamide and 72 mg of 3-[3-(4-bromophenyl)-3-hydroxypropyl]-1-(4-fluorophenyl)-4-(4-methoxyphenyl)-azetidin-2-one are prepared analogously to the synthesis of Example XXXI. The product is obtained as an amorphous solid.

Using the method described below, the activity of the compounds of the formula I according to the invention was examined:

Effect on Cholesterol Absorption +$^3$H-taurocholic Acid Excretion Using Fecal Excrement of Mice, Rats or Hamsters NMRI mice, Wistar rats, or Golden Syrian hamsters (in groups of n=4–6) are kept in metabolic cages, where they are fed with a standard diet (Altromin, Lage (Lippe)). The afternoon prior to the administration of the radioactive tracers ($^{14}$C-cholesterol), the feed is removed and the animals are adapted to grates.

Additionally, the animals are labeled s.c. with $^3$H-TCA (taurocholic acid) (for example 1 µCi/mouse up to 5 µCi/rat) 24 hours prior to the peroral administration of the test meal ($^{14}$C-cholesterol in Intralipid® 20, Pharmacia-Upjohn).

Cholesterol absorption test: 0.25 ml/mouse Intralipid® 20 (Pharmacia-Upjohn) ((spiked with 0.25 µCi of $^{14}$C-cholesterol in 0.1 mg of cholesterol) is administered perorally by gavage.

Test substances are prepared separately in 0.5% methylcellulose (Sigma)/5% Solutol (BASF, Ludwigshafen) or a suitable vehicle.

The administration volume of the test substance is 0.5 ml/mouse. The test substance is administered immediately prior to the test meal (Intralipid labeled with $^{14}$C-cholesterol) (cholesterol absorption test).

The feces are collected over a period of 24 h: fecal elimination of $^{14}$C-cholesterol and $^3$H-taurocholic acid (TCA) is determined after 24 hours.

The livers are removed and homogenized, and aliquots are incinerated in an oximate (Model 307, Packard) to determine the amount of $^{14}$C-cholesterol which had been taken up/absorbed.

Evaluation:

Feces Samples:

The total weight is determined, the sample is made up with water to a defined volume and then homogenized, and an aliquot is evaporated to dryness and incinerated in an oximate (Model 307 from Packard for the incineration of radioactively labeled samples): the amount of radioactive $^3$H—H$_2$O and $^{14}$C—CO$_2$ is extrapolated to the amount of $^3$H-taurocholic acid and $^{14}$C-cholesterol, respectively, that is excreted (dual isotope technique). The ED$_{200}$ values as dose from a dose-effect curve are interpolated as those doses at which the excretion of TCA or cholesterol is doubled, based on a control group treated at the same time.

Liver Samples:

The amount of $^{14}$C-cholesterol taken up by the liver is based on the administered dose. The EDN values are interpolated from a dose-effect curve as the dose at which the uptake of $^{14}$C-cholesterol by the liver is halved (50%), based on a control group.

The ED$_{50}$ values below demonstrate the activity of the compounds of the formula I according to the invention

| Example No. | ED$_{50}$ (liver) [mg/mouse] |
|---|---|
| II | 0.1 |
| III | 0.003 |
| XIII | 0.3 |
| XV | 0.01 |
| XVIII | 1.0 |
| XX | 0.03 |
| XXI | 1.0 |
| XXIV | 0.3 |
| XXV | 0.3 |
| XXX | 0.1 |

As can be seen from the table, the compounds of the formula I have very good cholesterol-lowering action. The compounds can thus be used to control cholesterol concentration. Such control can be by lowering the cholesterol concentration, or maintaining a desired level of cholesterol concentration.

Bioabsorption:

The bioabsorption of the compounds of the formula I can be examined using the Caco cell model (A. R. Hilgers et al., Caco-2 cell monolayers as a model for drug transport across the intestinal mucosa, Pharm. Res. 1990, 7, 902).

Below is a bioabsorption measurement for a reference compound:

|  | Reference structure | Example |
| --- | --- | --- |
| Apparent partition coefficient $P_{app}$ [cm/s] (according to Lit. Hilgers) | $4.88 \times 10^{-06}$ | |
| Estimated human bioabsorption | 100% | |

-continued

| | Reference structure | Example |
| --- | --- | --- |

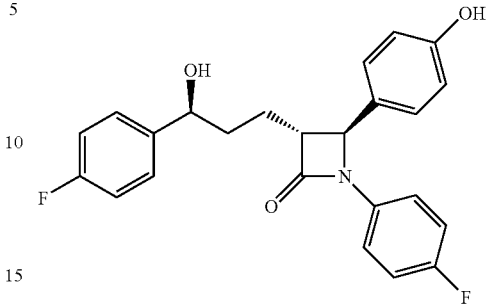

Reference structure:

Ezetimibe

We claim:

1. 1-(4-aminomethylphenyl)-3-[3-(4-fluorophenyl)-3-hydroxypropyl]-4-(4-methoxyphenyl)azetidin-2-one.

* * * * *